(12) United States Patent
Tsubouchi et al.

(10) Patent No.: US 8,263,347 B2
(45) Date of Patent: Sep. 11, 2012

(54) BIOMARKER FOR DIAGNOSIS OF LIVER DISEASE

(75) Inventors: Hirohito Tsubouchi, Kagoshima (JP); Hirofumi Uto, Kagoshima (JP); Takeshi Okanoue, Kyoto (JP); Yo-ichi Ishida, Miyazaki (JP); Yuko Sato, Miyazaki (JP); Masayuki Sudo, Kamakura (JP)

(73) Assignees: Miyazaki Prefectural Industrial Support Foundation, Miyazaki; Kagoshima University, Kagoshima (JP); Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/738,684

(22) PCT Filed: Oct. 20, 2008

(86) PCT No.: PCT/JP2008/068985
§ 371 (c)(1),
(2), (4) Date: Sep. 22, 2010

(87) PCT Pub. No.: WO2009/051259
PCT Pub. Date: Apr. 23, 2009

(65) Prior Publication Data
US 2011/0129859 A1 Jun. 2, 2011

(30) Foreign Application Priority Data

Oct. 18, 2007 (JP) .................................. 2007-270799
Jun. 3, 2008 (JP) .................................. 2008-145337

(51) Int. Cl.
*G01N 33/53* (2006.01)
(52) U.S. Cl. ........................................ 435/7.1; 436/518
(58) Field of Classification Search ........................ None
See application file for complete search history.

(56) References Cited

FOREIGN PATENT DOCUMENTS

| JP | 04110660 A | 4/1992 |
|---|---|---|
| JP | 2006300689 A | 11/2006 |
| JP | 2006308533 A | 11/2006 |
| WO | 2006/121892 A2 | 11/2006 |
| WO | 2007/022248 A2 | 2/2007 |

OTHER PUBLICATIONS

Violi et al. J. Clin. Pathol. 1986 vol. 39, p. 1003-1005.*
Mohammand et al. Am. J. Physio. Heart Cir. Physiol. 1998 vol. 275, p. H145-150.*
Bouhnik, et al., "Biochemical and physiological studies on two T-kinino species using monoclonal antibodies", Biochimica Et Biophysica Acta, Jul. 13, 1992, pp. 70-76, vol. 1122, No. 1.
Fujii, "Kan Shikkan Kanja ni Okeru Kessho Kallikrein-kinin-kei no Hendo to sono Rinshoteki Igi-Tokuni Alcohol-sei Kan Shogai o Chushin to shite", Japanese Journal of Gastroenterlogical Surgery, Mar. 5, 1985, pp. 450-458, vol. 82, No. 3.
Maejima, et al., "Kan Shikkan Kanja ni Okeru Kessei Hotaila Oyobi C3, C4 Tanpaku Ryo ni tsuite no Kento", Journal of Tokyo Women's Medical University, 1981, pp. 441-446, vol. 51, No. 4.
Ikeda, et al., "Chumoku sareru Jin Kanren Tanpaku-45 C4", Kidney and Dialysis, Dec. 25, 2006, pp. 750-752, vol. 61, No. 6.
Sato, et al., "Kessei Proteome Kaiseki de Dotei shita Kininogen Danpen wa Hi-Alcohol-sei Shibokan Shikkan de Zoka suru, Dai 44 Kai", The Japan Society of Hepatology Sokai Koen Yoshi, Apr. 2008, p. A163.
Cordova, et al., "Hageman factor, high molecular weight kininogen, and prekallikrein in chronic liver disease." J Clin Pathol, 1986, pp. 1003-1005, vol. 39.
Dumestre-Perard, et al., Complement C4 monitoring in the follow-up of chronic hepatitis C treatment, Clinical and Experimental Immunology, Jan. 2002, pp. 131-136, vol. 127, issue 1.
Hirofumu et al., "A Fragment of High Molecular Weight Kininogen is Upregulated in Patients With Non-Alcoholic Fatty Liver Disease" Hepatology, vol. 48, No. 4, p. 822A. Suppl. S (2008).
Fatty Liver: Approach to the Patient with Liver Disease: Merck Manual Professional; www.merckmanuals.com/professional/print/hepatic_and_biliary_disorders/appr..., Nov. 2, 2011.
Clinical Guideline for NASH-NAFLD, Chapters 1 (Definition and Classification of NAFLD) and 3 (Pathogenesis and Pathology of NAFLD), May 27, 2010.
Kanzo, *Liver*, vol. 50, pp. 741-747, 2009.

* cited by examiner

*Primary Examiner* — Jacob Cheu
(74) *Attorney, Agent, or Firm* — Browdy and Neimark, PLLC

(57) ABSTRACT

Disclosed are: a marker for the diagnosis of a liver disease, which can determine the disease in a simple manner; an antibody directed against the marker; a diagnostic agent; a diagnosis method; and a method for marker detection in blood or serum. Proteome analysis revealed that quantities of the full-length kininogen and three partial peptides thereof (sequence A: position-440 to position-456, sequence B: position-439 to position-456, and sequence C: position-438 to position-456) in sera of patients with non-alcoholic fatty liver disease are significantly different from those in sera of healthy individuals; and a diagnostic agent and a detecting method for the non-alcoholic fatty liver disease that can be conveniently used for medical examination are established. The use of a combination of a kininogen-based marker and a C4-based marker (the full length sequence or partial peptides thereof) enables identification of chronic hepatitis and an asymptomatic virus carrier, as well as non-alcoholic fatty liver disease.

16 Claims, 18 Drawing Sheets

(A) 1942m/z (B) 2079m/z (C) 2207m/z (A) Peak intensity vs. m/z
NAFLD patient
Healthy individual (B) Peak intensity vs. m/z
NAFLD patient
Healthy individual (C)

(a) 1942m/z (b) 2079m/z (C) 2207m/z (A) 1738m/z (B) 1896m/z (A)

(B)

(A)

(B)

(C)

BIOMARKER FOR DIAGNOSIS OF LIVER DISEASE

TECHNICAL FIELD

The present invention relates to a biomarker for diagnosis of liver diseases (hereinafter referred to as marker(s)), more specifically, to a marker, an antibody, a diagnostic agent, and a detecting method for discrimination between a non-alcoholic fatty liver disease (hereinafter referred to as "NAFLD"), chronic hepatitis, and an asymptomatic carrier (hereinafter referred to as "ASC").

BACKGROUND ART

In general, it is said that NAFLD includes simple steatosis (hereinafter, "SS") and non-alcoholic steatohepatitis (hereinafter referred to as "NASH"), which is developed from SS. NASH has a possibility to progress to poor prognosis diseases such as cirrhosis, and hepatocellular carcinoma. However, at present, there are no useful diagnostic markers for diagnosing NAFLD. NAFLD is usually diagnosed by ultrasonography, but pathological findings of liver biopsy are necessary for its correct diagnosis. The liver biopsy imposes a heavy burden on patients and lacks convenience. Accordingly, it is unsuitable for medical examination of lifestyle-related diseases. If NAFLD is detected at an earlier stage, NAFLD can be immediately prevented from progressing and can be treated, which is, needless to say, very advantageous.

Regarding a kininogen, Japanese Unexamined Patent Application Publication No. 04-110660 (Patent Literature 1) discloses a liver disease diagnostic agent composed of a kininogen/calpain complex. Patent Literature 1 states that the complex diagnostic agent is useful for diagnosing liver diseases such as chronic hepatitis, liver cirrhosis, hepatocellular carcinoma, hepatitis A, and fulminant hepatitis, but not NAFLD. Furthermore, there is no description about the use of full-length kininogen or a specific biological material derived from the kininogen as an NAFLD diagnostic marker.

C. Cordova, et al. (Non-Patent Literature 1) report on that the level of kininogen decreases in patients with chronic hepatitis or liver cirrhosis, compared to that in healthy individuals, but do not mention or suggest any relationship between hepatic steatosis (including NAFLD) and the kininogen.

Thus, a marker is desired for discrimination between, for example, chronic hepatitis, liver cirrhosis, and hepatocellular carcinoma that have been developed from NAFLD. A known marker of such a type is complement C4, which is a protein generated in the liver and present in the serum and gets involved in immunoreaction and prevention of infection. Japanese Unexamined Patent Application Publication No. 2006-300689 (Patent Literature 2), a report on the use of C4 as a liver disease marker, states that the marker can be detected in patients with chronic hepatitis or liver cirrhosis, but not in healthy individuals or that the marker can be detected in healthy individuals and patients with chronic hepatitis, but not in patients with liver cirrhosis. Patent Literature 2, however, does not mention the discrimination of healthy individuals, patients with NAFLD, and patients with chronic hepatitis, including ASCs of hepatitis virus, from one another. Furthermore, Japanese Unexamined Patent Application Publication No. 2006-308533 (Patent Literature 3) states that the presence or absence or the amounts of complement C4 and its partial peptides are different between healthy individuals and liver cancer patients and are therefore useful as markers for discriminating patients with liver cancer from healthy individuals. Patent Literature 3, however, does not mention the discrimination of healthy individuals, patients with NAFLD, patients with chronic hepatitis, and ASCs from one another at all.

Furthermore, Dumestre-Perard, et al. (Non-Patent Literature 2) report on a method for determining the results of treatment of chronic hepatitis caused by hepatitis C virus through monitoring the correlation between C4 and a rheumatoid factor during the process of treating with, for example, interferon or ribavirin, but do not mention the discrimination of healthy individuals, patients with NAFLD, patients with chronic hepatitis, and ASCs from one another at all.

Patent Document 1: Japanese Unexamined Patent Application Publication No. 04-110660
Patent Document 2: Japanese Unexamined Patent Application Publication No. 2006-300689
Patent Document 3: Japanese Unexamined Patent Application Publication No. 2006-308533
Non Patent Document 1: C Cordova, et al., "Hageman factor, high molecular weight kininogen, and prekallikrein in chronic liver disease", J Clin Pathol, 39, 1003-1005, (1986)
Non Patent Document 2: Dumestre-Perard, et al., Clin Exp Immunol, 127, 131-136, (2002)

DISCLOSURE OF THE INVENTION

Problems to be Solved by the Invention

It is an object of the present invention to provide a marker, an antibody, a diagnostic agent, and a detecting method that may be conveniently used for identification of NAFLD.

It is an object of the present invention to provide a marker, an antibody, a diagnostic agent, and a detecting method that may be conveniently used for identification of chronic hepatitis and an ASC.

It is an object of the present invention to provide a diagnostic agent and a detecting method that are suitable for the purpose of combined use of the above-mentioned markers.

Means for Solving the Problems

The present invention, which achieves the above-mentioned objects, includes the following aspects:

Aspect 1: A biomarker for identification of NAFLD, the biomarker comprising a full-length high-molecular-weight kininogen and/or a partial peptide derived from the highmolecular-weight kininogen, wherein the partial peptide derived from the high-molecularweight kininogen is any one of the following sequences A, B, and C:

```
sequence A:
Asn Leu Gly His Gly His Lys His Glu Arg Asp

Gln Gly His Gly His Gln (SEQ ID NO: 2), sequence B:
His Asn Leu Gly His Gly His Lys His Glu Arg Asp Gln Gly His Gly His Gln (SEQ ID NO: 3),
and sequence C:
Lys His Asn Leu Gly His Gly His Lys His Glu Arg Asp Gln Gly His Gly His Gln (SEQ ID NO: 4);
```

Aspect 2: The biomarker according to Aspect 1, wherein the full-length highmolecular-weight kininogen and/or the partial peptide derived from the high-molecularweight kininogen include a modified form thereof;

Aspect 3: An antibody for identification of NAFLD, the antibody recognizing at least one of the biomarkers according to Aspect 1 or 2 as an antigen;

Aspect 4: The antibody according to Aspect 3, wherein the antibody is a polyclonal antibody that is obtained by immunizing a rabbit with at least one selected from the group consisting of the full-length kininogen and the partial peptide of the sequence A, the partial peptide of the sequence B, and the partial peptide of the sequence C;

Aspect 5: The antibody according to Aspect 3, wherein the antibody is a monoclonal antibody that is obtained by immunizing a mouse with at least one selected from the group consisting of the full-length kininogen and the partial peptide of the sequence A, the partial peptide of the sequence B, and the partial peptide of the sequence C;

Aspect 6: A diagnostic agent for identification of NAFLD, the agent comprising at least one selected from the group consisting of the biomarkers according to Aspect 1 or 2 and the antibodies according to any of Aspects 3 to 5;

Aspect 7: A biomarker for identification of hepatitis and an ASC, the biomarker being complement C4 and/or a partial peptide derived from C4, wherein the partial peptide derived from C4 is at least one selected from the group consisting of C4a (SEQ ID NO:5), C4b (SEQ ID NO:6), C4c, and the following sequences D and E:

```
sequence D:
Asn Gly Phe Lys Ser His Ala Leu Gln Leu Asn

Asn Arg Gln Ile (SEQ ID NO: 7),
and sequence E:
Asn Gly Phe Lys Ser His Ala Leu Gln Leu Asn Asn Arg Gln Ile Arg (SEQ ID NO: 8);
```

Aspect 8: An antibody for identification of chronic hepatitis and an ASC, the antibody recognizing at least one of the biomarkers according to Aspect 7 as an antigen;

Aspect 9: The antibody according to Aspect 8, wherein the antibody is a polyclonal antibody;

Aspect 10: The antibody according to Aspect 8, wherein the antibody is a monoclonal antibody;

Aspect 11: A diagnostic agent for identification of chronic hepatitis and an ASC, the agent comprising at least one selected from the group consisting of the biomarker according to Aspect 7 and the antibodies according to any of Aspects 8 to 10;

Aspect 12: A diagnostic agent for identification of NAFLD, chronic hepatitis, and an ASC, the agent comprising a combination of at least one of the biomarkers, the antibodies, and the diagnostic agent according to any of Aspects 1 to 6 and at least one of the biomarker, the antibodies, and the diagnostic agent according to any of Aspects 7 to 11;

Aspect 13: A detecting method for identification of NAFLD, the method using at least one of the biomarkers, the antibodies, and the diagnostic agent according to any of Aspects 1 to 6;

Aspect 14: A detecting method for identification of chronic hepatitis and an ASC, the method using at least one of the biomarkers, the antibodies, and the diagnostic agent according to any of Aspects 7 to 11;

Aspect 15: A detecting method for identification of NAFLD, chronic hepatitis, and an ASC, the method including a combination of the detecting method according to Aspect 13 and the detecting method according to Aspect 14;

Aspect 16: The detecting method according to any of Aspects 13 to 15, the method using an antibody that recognizes the high-molecular-weight kininogen in a sample but does not recognize any of the partial peptide of the sequence A, the partial peptide of the sequence B, and the partial peptide of the sequence C;

Aspect 17: The detecting method according to Aspect 16, wherein the detection is performed by ELISA; and Aspect 18: The diagnostic agent according to Aspect 6 or 12, wherein the antibody recognizes the high-molecular-weight kininogen in a sample but does not recognize any of the partial peptide of the sequence A, the partial peptide of the sequence B, and the partial peptide of the sequence C.

Hereinafter, in the present invention, the term "kininogen-based marker" means a full-length kininogen, a partial peptide thereof consisting of the sequence A, B, or C (hereinafter referred to as partial peptide A, B or C), or a partial peptide belonging to the kininogen D5 region described below, unless specifically stated otherwise. In addition, in the present invention, the term "C4-based marker" means complement C4 including C4A or C4B, C4a, C4b, or C4c, or a partial peptide consisting of the sequence D or E (hereinafter referred to as partial peptide D or E), unless specifically stated otherwise.

In addition to the above aspects, the present invention may preferably include the following embodiments:

a) A kininogen-based marker comprising the full-length high-molecular-weight kininogen according to Aspect 1 or 2, which decreases or disappears in a biological specimen collected from a patient with NAFLD compared to that from a healthy individual;

b) A kininogen-based marker being at least one selected from the group consisting of the partial peptides A, B, and C according to Aspect 1 or 2, used for determining that a subject is suffering from NAFLD when the marker increases in a biological specimen collected from a patient with NAFLD compared to that from a healthy individual;

c) A detecting method using a kininogen-based marker, in which a combination of the full-length high-molecular-weight kininogen with at least one selected from the group consisting of the partial peptides A, B, and C is used, and a subject is determined as suffering from NAFLD when the full-length marker decreases and at least one selected from the group consisting of the partial peptides A, B, and C increases compared to those in a healthy individual;

d) A C4-based marker contained in the full-length complement C4 according to Aspect 7, which decreases or disappears in a biological specimen from a patient with chronic hepatitis or an ASC compared to that in a healthy individual or a patient with any other liver disease;

e) A C4-based marker derived from complement C4, being at least one selected from the group consisting of C4a, C4b, and C4c and the partial peptides D and E according to Aspect 7, used for determining that a subject is suffering from chronic hepatitis or is an ASC when the marker increases in a biological specimen from a patient with chronic hepatitis or an ASC compared to that from a healthy individual;

f) A detecting method using a C4-based marker, in which a combination of the full-length complement C4 with at least one selected from the group consisting of the partial peptides C4a, C4b, C4c, D and E derived from the C4 is used, and a subject is determined to be suffering from chronic hepatitis or is an ASC when the C4-based marker contained in the full-length decreases and at least one selected from the group consisting of partial peptides C4a, C4b, C4c, D, and E increases compared to those in a healthy individual;

g) A detecting method using both the kininogen-based marker and the C4-based marker for identification of NAFLD, chronic hepatitis, and an ASC according to Aspect 14, comprising detecting a decrease or disappearance of the full-length high-molecular-weight kininogen and/or an increase or expression of at least one of the partial peptides A, B, and C; and detecting a decrease of the C4-based marker contained in the full-length C4 and an increase or expression of at least one of the partial peptides C4a, C4b, C4c, D, and E derived from C4;

h) A detecting method using both the kininogen-based marker and the C4-based marker for identification of a healthy individual, a patient with NAFLD, a patient with chronic hepatitis, and an ASC according to Aspect 14, comprising detecting an increase or expression of the full-length high-molecular-weight kininogen and/or a decrease or disappearance of at least one of the partial peptides A, B, and C; and detecting an increase or expression of the C4 and/or a decrease or disappearance of at least one of the partial peptides C4a, C4b, C4c, D, and E; and i) A detecting method using both the kininogen-based marker and the C4-based marker for identification of a healthy individual, a patient with NAFLD, a patient with chronic hepatitis, and an ASC according to Aspect 14, comprising detecting an increase or expression of the full-length high-molecular-weight kininogen and/or detecting a decrease or disappearance of at least one of the partial peptides A, B, and C; and also detecting a decrease or disappearance of the C4 and/or an increase or expression of at least one of the partial peptides D and E.

Advantages of the Invention

The present invention is advantageous in that not only diagnosis of NAFLD but also diagnosis of progress thereafter can be expected.

(1) Since the level of expression of the kininogen-based marker is largely different between patients with NAFLD and healthy individuals, NAFLD may be conveniently and correctly diagnosed without liver biopsy imposing heavy burden on patients.

(2) Since the partial peptides A, B, and C of the kininogen include a large number of polar amino acids in their sequences and are thereby excellent in antigenicity, useful antibodies may be easily produced, and a kit thereof may be produced. In particular, the partial peptide C is excellent in recognition by an antibody and is therefore preferred.

(3) This enables insurance medical care for many people in pre-disease conditions, including prevention of lifestyle-related diseases such as metabolic syndromes, as a result.

(4) A multi-marker system composed of a combination of the kininogen-based marker and the C4-based marker enables diagnosis of the progress of a patient with NAFLD to chronic hepatitis or detection of an ASC, and, thereby, it is easy to determine a treatment principle according to the progress of a liver disease at an early stage.

BEST MODE FOR CARRYING OUT THE INVENTION

Figure 1:
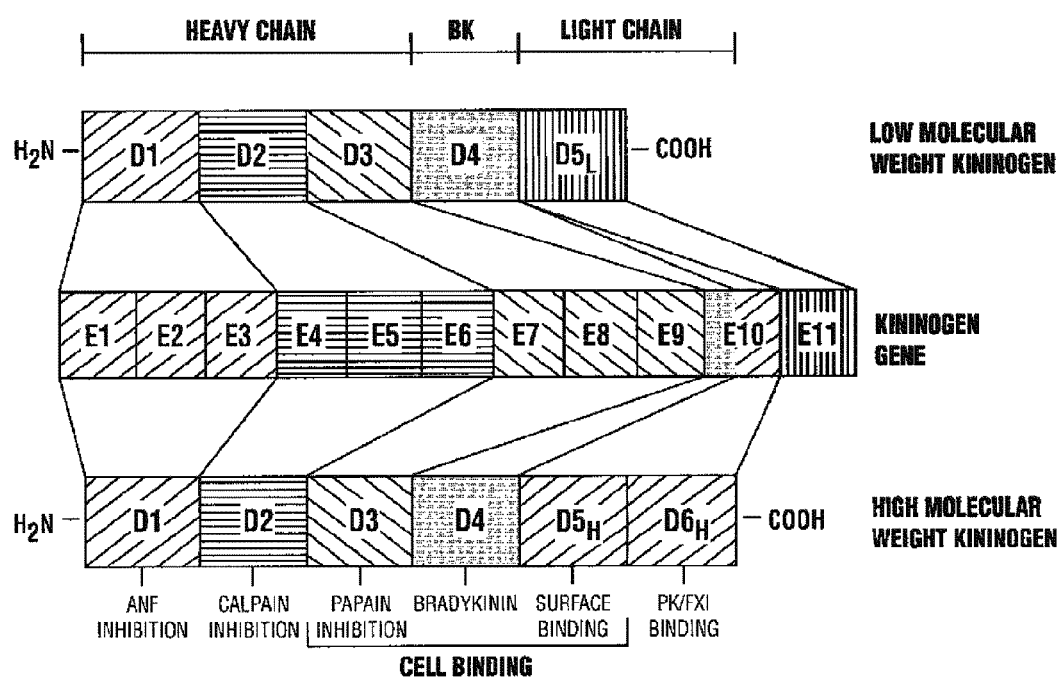
FIG. 1 is a schematic diagram illustrating domain structures of amino acid sequences of kininogens.

Full-length kininogen or its partial peptide includes post-translational modified forms of a high-molecular-weight kininogen, such as glycosylated forms. That is, the full-length high-molecular-weight kininogen is a protein consisting of a sequence of 644 amino acids shown in Sequence Listing 1. The kininogen gene contains 11 exons (E1 to E11) and, as shown in FIG. 1, are roughly classified into a high-molecular-weight kininogen and a low-molecular-weight kininogen due to a difference in splicing in transcription (Robert W. Colman, et al., "Contact System: A Vascular Biology Modulator With Anticoagulant, Profibrinolytic, Antiadhesive, and Proinflammatory Attributes", Blood, 90(10), 3819-3833, (1997)). The high-molecular-weight kininogen is a kininogen (644 amino acids: about 71 kDa, its glycosylated form: about 120 kDa) of Accession No. P01042 (SwissProt: Expercy) and consists of six functional domains (D1 to D6), whereas the low-molecular-weight kininogen consists of five domains (D1 to D5). In the both kininogens, D1 to D3 transcribed and translated from the same exons (E1 to E9) have the same amino acid sequence, while their sequences from D4 to the C-terminal side are different from each other because of a difference in mRNA splicing. In many cases, these kininogens include their post-translational modified forms, such as glycosylated forms. The partial peptides of the present invention have sequences A, B, and C as shown in Sequence Listings 2 to 4, and they are peptides which belong to the D5 region of the high-molecular-weight kininogen.

[Antibody for Detecting Markers]

In the identification of NAFLD according to the present invention, the above-mentioned full-length kininogen as well as partial peptides A, B, and C in sera may be directly used as markers. However, it is convenient and desirable to produce an antibody recognizing such markers by a common method and use it for diagnosis. The antibody may be produced by a known technology. Examples of the antibody include, but are not limited to, a polyclonal antibody, a monoclonal antibody, an F(ab) fragment, an Fv fragment, a single-chain antibody, a chimera antibody, a humanized antibody, and a Fab expression library and also include an antigen-binding protein. The monoclonal antibody is preferred in order to specifically recognize the kininogen.

The polyclonal antibody of the present invention is produced by administering the full-length kininogen or the partial peptide A, B, or C together with an immune-adjuvant to a host animal, such as rabbit, mouse, rat, guinea pig, or goat, for immunization. According to need, the immunogen may be conjugated to a high-molecular-weight carrier and be used for immunization. The immunization may be performed by, for example, repeating intracutaneous administration to many sites or direct administration to lymph nodes. Through the immunization, the IgM class is mainly produced in the primary immune response, and the IgG class is mainly produced in the secondary immune response. In order to extract the produced antibodies, a serum separated from the collected blood is subjected to ammonium sulfate precipitation according to need and then purification. The purification may be performed by dialysis, gel filtration, Protein A/G column chromatography, or antigen column chromatography.

The monoclonal antibody used in the method of the present invention can be prepared by a common method that includes immunizing a mouse with the full-length kininogen or peptide C of the present invention, fusing antibody-producing cells with myeloma cells, selecting a hybridoma that produces an anti-kininogen monoclonal antibody from the resulting hybridomas, and collecting the monoclonal antibody produced by culturing the hybridoma.

A typical method for producing a monoclonal antibody will be described below. A monoclonal antibody can be prepared by producing hybridomas through cell fusion of antibody-producing cells obtained from an animal immunized with an antigen and myeloma cells, and selecting a clone that produces an antibody that specifically recognizes the antigen from the resulting hybridomas.

The antigen used for immunization of an animal is the full-length kininogen or the partial peptide A, B, or C. The antigen is administered to a host animal such as mouse, rat, guinea pig, horse, monkey, rabbit, goat, sheep, or pig. Other immunized animals such as chicken can be also used. The immunization may be performed by any known method, but is mainly performed by, for example, intravenous injection, intracutaneous injection, or intraperitoneal injection. The immunization interval is not particularly limited and ranges from several days to several weeks, and immunization is preferably performed at intervals of 4 to 21 days.

Antibody-producing cells are collected after a predetermined period from the final immunization. Examples of the antibody-producing cells include spleen cells, lymph node cells, and peripheral blood cells. Spleen cells are usually used. The antigen is used, for example, in an amount of 100 µg per mouse in each immunization.

The antibody titer in blood of an immunized animal or the antibody titer in culture medium supernatant of antibody-producing cells is measured for confirmation of the immune response level of the immunized animal or selection of a target hybridoma from the cells after cell fusion treatment. Examples of the method for detecting the antibody include known assays such as enzyme immunoassay (EIA), radioimmunoassay (RIA), and enzyme-linked immunosorbent assay (hereinafter referred to as "ELISA").

The myeloma cells to be fused with the antibody-producing cells are derived from various animals such as mouse, rat, and human, and a cell line that is usually available to those skilled in the art is used. Cell lines having the following characteristics are used: the lines have drug resistance, cannot survive in a selection medium (for example, HAT medium) in their unfused state, and can survive in their fused state. In general, an 8-azaguanine resistant line is often used, and this cell line is deficient in hypoxanthine-guanine-phosphoribosyltransferase and thus cannot grow in a hypoxanthine-aminopterin-thymidine (HAT) medium.

Examples of the myeloma cell include P3x63Ag8.653, P3x63Ag8U.1, NS-1, MPC-11, SP2/0, F0, S194, and R210.

The antibody-producing cell may be obtained from, for example, a spleen cell or a lymph node cell. That is, the desired antibody-producing cell is prepared by extracting or collecting, for example, the spleen or the lymph node from an animal such as mentioned above, fracturing the tissue, suspending the resulting homogenate in a medium or buffer such as PBS, DMEM, or RPMI-1640, and subjecting the suspension to filtration through a stainless mesh or the like and then centrifugation.

Then, the myeloma cell and the antibody-producing cell are fused. The cell fusion is performed by bringing the myeloma cell into contact with the antibody-producing cell in a medium for culturing animal cells, such as an MEM, DMEM, or RPMI-1640 medium, for example, at a mixing ratio of 1:1 to 1:10 in the presence of a fusion-accelerating agent at 30 to 37° C. for 1 to 15 minutes. In order to accelerate the cell fusion, a fusion accelerating agent or a fusing virus, such as a polyethylene glycol or polyvinyl alcohol having an average molecular weight of 1000 to 6000 or Sendai virus, may be used. In addition, the antibody-producing cell and the myeloma cell may be fused using a commercially available cell fusion apparatus utilizing electric stimulation (for example, electroporation).

The intended hybridoma is selected from the cells after cell fusion treatment. The selection is performed by, for example, selective proliferation of cells using a selection medium. That is, the cell suspension is diluted with an appropriate medium and then is spread on a microtiter plate. A selection medium (such as HAT medium) is added to each well, and then, the cells are cultured by appropriately replacing the selection medium. As a result, survived cells are obtained as hybridomas.

The screening of the hybridoma is performed by, for example, a limiting dilution method or a fluorescence-activated cell sorting method, in order to obtain a monoclonal antibody-producing hybridoma finally. Examples of the method for harvesting the monoclonal antibody from the resulting hybridoma include usual cell culturing and ascitic fluid formation. In the cell culturing, the hybridoma is cultured, for example, in a medium for culturing animal cells, such as RPMI-1640 or MEM containing 10 to 20% fetal bovine serum, or a serum-free medium, under usual culture conditions (for example, at 37° C., 5% $CO_2$) for 2 to 14 days, and the antibody is collected from the culture supernatant. In the ascitic fluid formation, the hybridoma is administered in the abdominal cavity of the same type animal as a mammal from which the myeloma cells are derived, and a large amount of the hybridoma is proliferated. Then, the ascitic fluid or the serum is collected one to four weeks later.

In the extraction of the antibody, if purification of the antibody is necessary, any known purification process such as ammonium sulfate precipitation, ion exchange chromatography, affinity chromatography, or a combination thereof is selected.

The anti-kininogen antibody of the present invention may also be selected from commercially available or publicly reported polyclonal or monoclonal antibodies recognizing the kininogen of the present invention or its biological decomposition product, for example, the partial peptide A, B, or C, in addition to the antibody produced by the above-mentioned method of the present invention. Alternatively, an antibody may be newly produced by the above-mentioned method.

The polyclonal antibody is preferably produced by immunizing a rabbit with at least one selected from the group consisting of the full-length kininogen, the partial peptide A, the partial peptide B, and the partial peptide C. For example, preferred are rabbit-anti-human-HMW-kininogen (RABBIT ANTI HUMAN HMW-KININOGEN 5575-4957, manufactured by AbD Serotec) and rabbit-anti-human-kininogen that is specific to K438-Q456 peptides (Sigma-Aldrich Japan special order product). The monoclonal antibody is preferably produced by immunizing a mouse with at least one selected from the group consisting of the full-length kininogen, the partial peptide A, the partial peptide B, and the partial peptide C. Specifically, preferred are (mouse-monoclonal) HMW Kininogen Light Chain antibody [1.B.709] (manufactured by GeneTex Inc.) and (mouse-monoclonal) Anti-human-kininogen/Kininostatin antibody (manufactured by R&D Systems) specific to K438-5531 peptides.

A diagnostic agent may be prepared using the above-described marker of the present invention by a common process. Furthermore, a kit with the above-described various antibodies may be used as for convenient diagnosis.

In the present invention, a comparison was made between healthy individuals and NAFLD patients with respect to peak intensities in spectra of proteomic analysis on sera, and candidates of markers for NAFLD diagnosis are determined on the basis of statistic test values or absolute values of peak intensities or a significant difference therebetween. The NAFLD diagnostic marker in the present invention is a protein or a partial peptide identified from the thus selected marker candidates. Various well-known methods of qualitative and quantitative determination of protein for those skilled in the art may be used without particular limitation. For example, proteomic analysis involving gel electrophoresis such as two-dimensional electrophoresis, shotgun analysis by LC-MS, or a method using an antibody against a specific biological material may be used. Specifically, immunochemical detection processes using an antibody, for example, ELISA, radioimmunoassay (RIA), a method using an antibody chip (protein chip in which antibodies are densely immobilized on a surface of a solid-phase such as glass), Western blotting, or immunostaining of a tissue section, may be used. Furthermore, in mass spectrometric (MS) detection, for example, after fractionation on a chip or with a column, which will be described in detail below, the protein on the chip or in the eluate from the column is subjected to molecular weight measurement by MS. Liquid chromatography or dot blotting may also be employed.

Regarding the full-length kininogen (SEQ ID NO:1) and its partial peptides A, B, and C (SEQ ID NOs:2-4), which serve as the NAFLD diagnostic markers according to the present invention, the detection, selection, and identification thereof will be described below.

Sera of healthy individuals or patients with NAFLD are prepared by leaving the collected blood to stand or centrifuging the blood. In order to detect the protein or the partial peptide in the sera, a ClinProt system (Bruker Daltonics) or a Protein Chip system (Bio-Rad) is used. In these systems, exchangers having surfaces modified with various functional groups, for example, a cation exchanger and a copper-ion exchanger (IMAC-Cu) may be used alone or in combination. These exchangers can capture proteins and partial peptides having affinities to the functional groups.

Preferably, the ClinProt system is used together with ClinProt Profiling Kit 100 MB-WCX (Bruker Daltonics, hereinafter referred to as "WCX beads"), which is a bead type cation exchanger exclusive for the system. The captured proteins and partial peptides are used as test specimens and subjected to mass spectrometry to obtain peaks and peak intensities on a spectrum.

The WCX beads are used in accordance with the manual of the kit. First, the WCX beads are mixed with the prepared serum. The beads and the WCX binding solution provided in the kit are mixed in a washing vessel, for example, in a PCR tube, and the serum is added thereto, followed by leaving to stand (incubation) for a predetermined time. After the leaving to stand, the supernatant is removed using a pipette or any other tool. The WCX beads are washed, usually, two or more times to give a ClinProt eluate.

The resulting ClinProt eluate is mixed with, for example, a mixed solution (hereinafter referred to as "CCA solution") of α-cyano-4-hydroxycinamic acid (Bruker Daltonics, hereinafter referred to as "CCA") and an organic solvent. A predetermined amount of the CCA solution is placed dropwise on a thin film, followed by leaving to stand for a predetermined time for crystallizing the proteins and the partial peptides in the eluate and CCA to give a test specimen for mass spectrometry. From the viewpoint that the target protein in the test specimen is not required to be subjected to complicated processes such as purification and can be directly identified by MS/MS ion search, a peak intensity of 3000 m/z or less is desirable.

Also, in cases of other protein chip systems, the same procedures are basically performed in accordance with their manuals. Examples of the exchanger include a cation exchange chip, a reversed-phase chip, and a metal modify chip, which may be used alone or in combination. The concentration of the serum to be treated with a protein chip is preferably 1% (vol/vol) or more from the viewpoint of obtaining a satisfactory MS/MS spectrum. The peak sensitivity may be improved by controlling the concentration of the serum to be treated.

The ionization principle employed in the mass spectrometry is preferably matrix-assisted laser desorption/ionization (hereinafter referred to as "MALDI") from the viewpoint of convenience in sample preparation. The mass separation principle employed is preferably a time-of-flight type (hereinafter referred to as "TOF"). Therefore, a preferred mass spectrometer is a MALDI-TOF-MS, and more specifically, an Autoflex TOF-TOF (Bruker Daltonics, hereinafter referred to as "Autoflex") or Ultraflex TOF-TOF apparatus (Bruker Daltonics). The detecting procedure may be either a linear mode or a reflector mode, and the linear mode is preferred from the viewpoint of detection sensitivity. In addition, a protein chip system consisting of a protein chip and a surface-enhanced time-of-flight mass spectrometer (Bio-Rad, SELDI-TOF-MS, hereinafter referred to as "SELDI") may be used.

For example, in the use of Autoflex, first, the measurement is performed in the linear mode to obtain a mass spectrum. The linear mode measurement, as shown in Table 1 of Example 1 described below, produces a large number of peaks having different intensities between a healthy individual serum and an NAFLD patient serum. In the present invention, marker candidate proteins and partial peptides are selected from these peaks based on a statistical test, the absolute values of the peak intensities, or combination thereof. In comparison of a plurality of mass spectra, peaks having m/z values that are in agreement with each other within an error of 0.1% may be recognized as being derived from the same molecule. The following three partial peptides having sequences identified in the present invention are candidates of the NAFLD diagnostic markers of the present invention selected in accordance with the above-mentioned criteria: partial peptide A (approximately 1942 m/z), partial peptide B (approximately 2079 m/z), and partial peptide C (approximately 2207 m/z).

In the present invention, the kininogen that is a candidate of these markers is identified by, for example, MS/MS analysis. The test specimen for the identification may be prepared by a thin film technique. For example, a saturated acetone solution of CCA is applied to the anchor surface of an anchor chip in advance to form a thin film therefrom. Then, about 1 μL of a WCX bead eluate of an NAFLD patient serum is placed dropwise on the thin film, followed by leaving to stand for about 5 minutes to crystallize the proteins and partial peptides in the eluate and CCA. The crystal is then washed with 3 μL of 0.1% trifluoroacetic acid (hereinafter referred to as "TFA") around three times for desalination.

In acquisition of an MS/MS spectrum, for example, high-accuracy measurement is performed in the reflector mode of Autoflex to obtain molecular weights of a target peak (parent ion) and their fragments (ions of partial peptides). The correction (calibration) of the molecular weight may be performed by peptide calibration standard 2 (Bruker Daltonics, hereinafter referred to as "PCS-2"). Based on the observed MS/MS spectrum, a peak list of the parent ions and their fragment ions may be made using BioTools (Bruker Daltonics), and these peaks may be identified by MS/MS ion search of Mascot search (Matrix Science).

Figure 3:
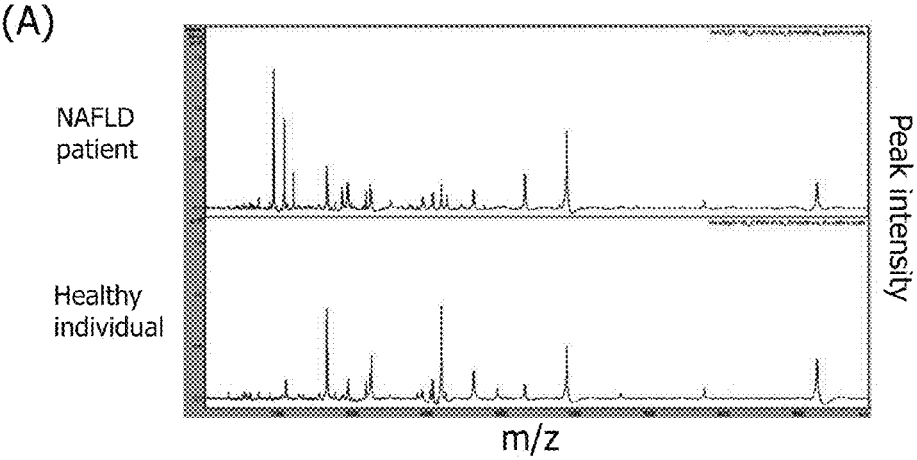
FIG. 3 includes graphs showing spectral comparison of patients with NAFLD and healthy individuals using ClinProt; Graph (A) shows typical spectral patterns of a patient with NAFLD and a healthy individual measured by a linear mode of Autoflex; Graph (B) shows an enlarged view of the region near 1800 to 2300 m/z in Graph (A), and three peaks observed in the patient with NAFLD are peaks at 1942 m/z, 2079 m/z, and 2207 m/z from the left; the vertical axis represents peak intensity, and the horizontal axis represents molecular weight in Graphs (A) and (B); and Graph (C) plots peak intensities of the patients with NAFLD and the healthy individuals at 1942 m/z (a), 2079 m/z (b), and 2207 m/z (c).
Figure 3:
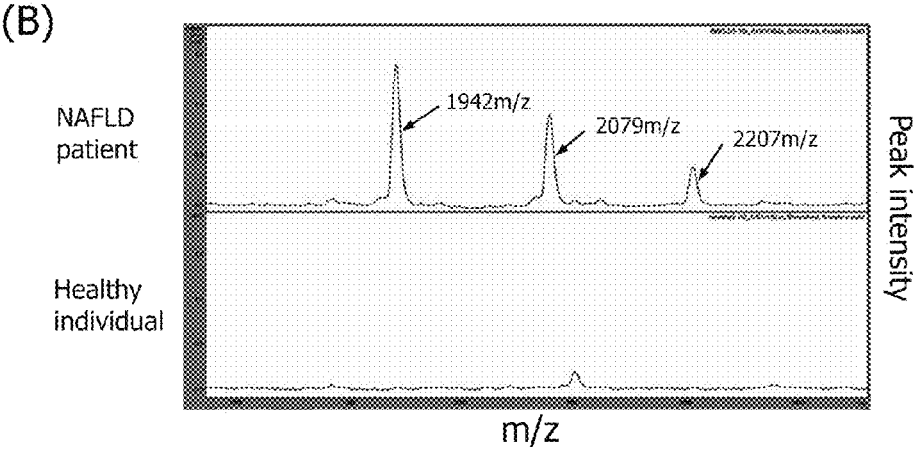
Figure 3:
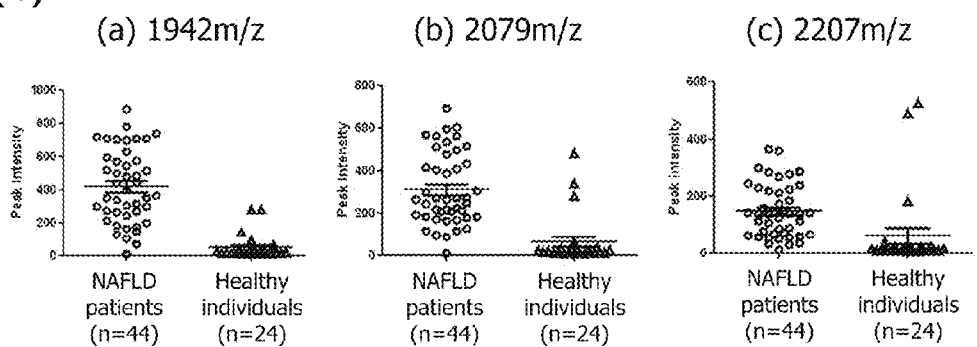

As shown in FIG. 3, in addition to the parent ion peaks (1942, 2079, and 2207 m/z), a large number of ion peaks of partial peptides are generally detected. A peak list is prepared based on these spectrum, and the partial peptides come from the peaks are identified by MS/MS ion search. As a result, it was revealed that all the peak (A) at 1942 m/z, the peak (B) at 2079 m/z, and the peak (C) at 2207 m/z of the three candidates of the NAFLD diagnostic markers of the present invention correspond to the following partial peptides belonging to the domain D5, which is a part of the high-molecular-weight kininogen.

```
Sequence A:
Asn Leu Gly His Gly His Lys His Glu Arg Asp

Gln Gly His Gly His Gln (SEQ ID NO: 2)
(440th to 456th SEQ ID NO: 1),

Sequence B:
His Asn Leu Gly His Gly His Lys His Glu Arg

Asp Gln Gly His Gly His Gln (SEQ ID NO: 3)
(439th to 456th SEQ ID NO: 1), and

Sequence C:
Lys His Asn Leu Gly His Gly His Lys His Glu

Arg Asp Gln Gly His Gly His Gln (SEQ ID NO: 4)
(438th to 456th SEQ ID NO: 1).
```

The diagnosis of NAFLD using the marker of the present invention may be performed by the following process. For example, in the case of mass spectrometry, a threshold value is set using a cut-off value calculated by adding the standard deviation to the average of the peak intensities of healthy individuals and is used for diagnosing whether a subject is NAFLD or not. In the cases where each partial peptide A, B, or C of the kininogen is used alone as a marker for diagnosing NAFLD, diagnosis with high sensitivity (correct-positive rate) and specificity (correct-negative rate) may be performed through determination of the sensitivity and the specificity by a common method. For example, as shown in Table 1, 40 subjects among the 44 NAFLD subjects were diagnosed as NAFLD (sensitivity: 90.99%), and 21 subjects among the 24 healthy individual subjects were diagnosed as healthy individuals (specificity: 87.5%), using the peak at 1942 m/z.

In addition, in the present invention, a combination of two or more of the partial peptides A, B, and C of the kininogen as a multimarker enables more correct diagnosis of NAFLD and grasp of its condition. Furthermore, multimarker diagnosis by a combination with an NAFLD diagnostic marker other than the partial peptides A, B, and C of the present invention or combined diagnosis by a combination with another blood or serum test results is also possible.

In particular, the kininogen partial peptides A, B, and C of the present invention are assumed to be generated by decomposition of the full-length kininogen with the progress of NAFLD, as shown in the analytical results of the decomposition pattern of the kininogen in "[3] Decomposition of full-length kininogen in NAFLD patient serum" in Example 1 described below. This suggests that the use in a combination with the full-length kininogen enables correct diagnosis of NAFLD or grasp of a progress in its condition by an increase in at least one of the partial peptides A, B, and C and a decrease in the full-length kininogen. Since NAFLD may be regarded as an initial stage that progresses to liver cirrhosis and hepatocellular carcinoma, the multimarker may be used as an early diagnosis marker of hepatocellular carcinoma.

As shown by C. Cordova, et al. (Non-Patent Literature 1), since the full-length kininogen tends to decrease with progress of liver cirrhosis or hepatocellular carcinoma, the extent of progress from NAFLD to liver cirrhosis or hepatocellular carcinoma may be diagnosed by combination with the partial peptide A, B, or C of the present invention or another marker or another test result.

In the present invention, at least one protein and/or partial peptide of the full-length kininogen and the partial peptides may be used as the marker. Patients with NAFLD and healthy individuals may be discriminated with high accuracy from each other using, preferably two or more types, more preferably three or more types or four types of the protein and/or the partial peptides. In such a case, the combination may be of the full length and the partial peptide or of the partial peptides only. Thus, NAFLD may be more correctly detected using the full length and/or the partial peptide as the marker, and the degree of its progress may be accurately determined.

In addition, in the present invention, the marker may be quantitatively measured or its presence or absence may be determined by qualitative measurement. The use of the full-length kininogen or the partial peptide as a marker enables correct diagnosis with a protein/partial peptide profile prepared based on the correct level obtained by quantitative measurement of the marker. Use of an increased number of markers enables correct diagnosis by qualitative measurement of the makers to obtain a protein/partial peptide profile regarding the presence or absence of each maker.

As described above, recently, methods by multimarker systems have been proposed for detecting various types of diseases with high accuracy. The present invention using these antibodies may be also widely applied to such assay or measurement of blood or serum for detection of the presence or absence or the amount of an NAFLD diagnostic marker in human blood or serum. In this point, it is advantageous to use at least one of the kininogen-based markers in combination with a marker of another system. For example, a combination, as a multimarker, with the below-described C4-based marker including a series of specific biological materials relating to C4 found by the present inventor as markers may discriminate between a healthy individual, a patient with NAFLD, a patient with chronic hepatitis, and an ASC.

Figure 2:
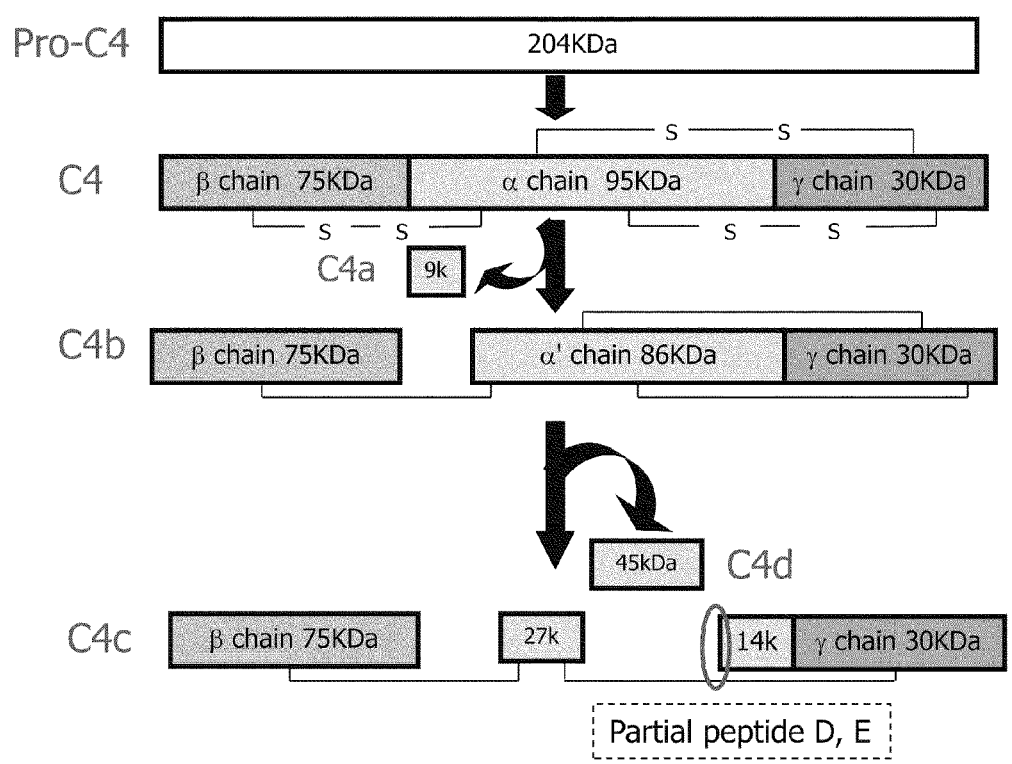
FIG. 2 is a schematic diagram illustrating domain structures of complement C4 (C4A and C4B) and its decomposition products.

The term "C4" means the fourth component of the complement (C4 fraction of complement) and is a glycoprotein with a molecular weight of 198000 and a structure in which three polypeptide chains are coupled with disulfide bonds by processing after translation. Among the complement components in blood, C4 is abundant next to C3. Known isoforms of C4 include, for example, C4A with Accession No. P0C0L4 (SwissProt: Expercy) and C4B with Accession No. P0C0L5 (SwissProt: Expercy). The C4 gene is located together with C2 and factor B genes on an HLA region of chromosome 6 and is synthesized as a single chain proC4 in a liver cell, monocyte, or macrophage, and is secreted as C4 after binding with sugar chains and fragmentation to three chains. It is said that C4A is involved in removal of pathogens while C4B is mainly involved in disinfection and cytoclasis (for example, hemolysis). In the description of the present invention, C4 encompasses these two isoforms, unless specifically stated otherwise. The sequences of C4 (C4A and C4B) and C4A and C4B, which are decomposition products of the C4 as shown in FIG. 2 (decomposition process of C4), are shown in Sequence Listings 5 and 6. C4, as well as C1 and C2, is called an initial response complement component in a classical pathway and plays an important role in transmission of the activity of C1 to C3. After C1 is activated, C4 is decomposed to C4a and C4b. C4 is also similarly decomposed by various serine proteases other than C1. The C4b produced as a result of the activation of C4 forms, for example, (1) C4bC2 by binding with C2, (2) a conjugate with a C4b-binding protein (C4bp), or (3) a conjugate with a C4b receptor (the same as CR1). The C4a is released to a liquid phase and shows an anaphylatoxin activity. By the mechanism (1), the activity is transmitted, and the C4b is decomposed, through several reactions, to C4c, which is released to a liquid phase, and C4d, which remains on a cell membrane. As a result, the C4b activity is lost.

In the present invention, C4 or the above-mentioned partial peptide as the C4-based marker is used in combination with a kininogen-based marker, so that a healthy individual, a patient with NAFLD, a patient with chronic hepatitis, and an ASC are determined through comparison of the levels thereof in a patient to those in a healthy individual. Various known methods may be used for such determination. That is, a protein or peptide may be quantitatively determined for the measurement of C4, C4a, C4b, or C4c by the above-mentioned various detecting methods.

The partial peptides D and E derived from C4 according to the present invention are identified by preparing a test specimen for the identification and then subjecting the specimen to MS/MS analysis (below-described Example 2), as in the partial peptides of the kininogen.

Accordingly, a large number of peaks having different intensities were found in sera of a healthy individual, a patient with NAFLD, a patient with chronic hepatitis, and an ASC. In the present invention, proteins and partial peptides are selected as marker candidates from these peaks based on a statistical test or the absolute values of peak intensities or combination of the both. In the case of comparison of a plurality of mass spectra, peaks having m/z values that are in agreement with each other within an error of 0.1% may be recognized as being derived from the same molecule. The following partial peptides are candidates of the marker for discriminating between liver diseases of the present invention selected in accordance with such criteria.

```
Sequence D:
Asn Gly Phe Lys Ser His Ala Leu Gln Leu Asn

Asn Arg Gln Ile,
and

Sequence E:
Asn Gly Phe Lys Ser His Ala Leu Gln Leu Asn

Asn Arg Gln Ile Arg.
```

Figure 16:
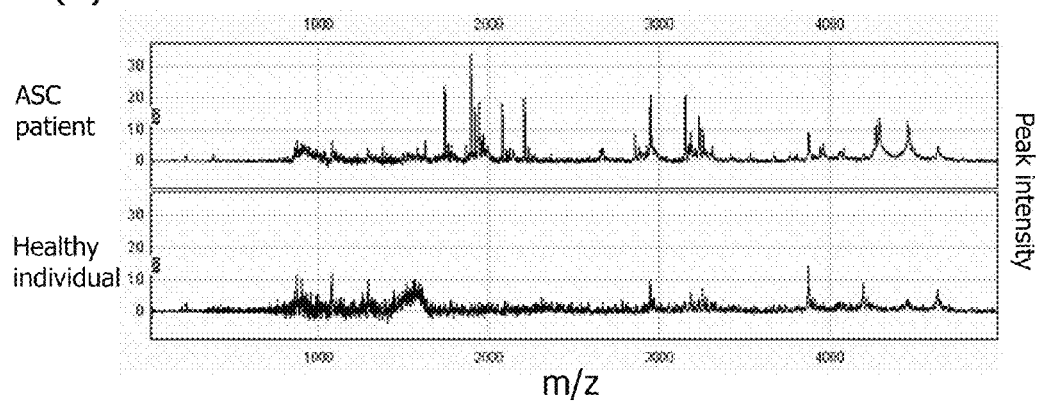
FIG. 16 includes graphs showing spectral comparison of ASCs and healthy individuals using a protein chip; Graph (A) shows typical spectral patterns of an ASC and a healthy individual measured by SELDI; Graph (B) shows an enlarged view of the region near 1600 to 2100 m/z in Graph (A), and two peaks observed in the ASC are peaks at 1738 m/z and 1896 m/z from the left; the vertical axis represents peak intensity; and the horizontal axis represents molecular weight in Graphs (A) and (B); and Graph (C) plots peak intensities of the ASCs and the healthy individuals at 1738 m/z (a) and 1896 m/z (b).
Figure 16:
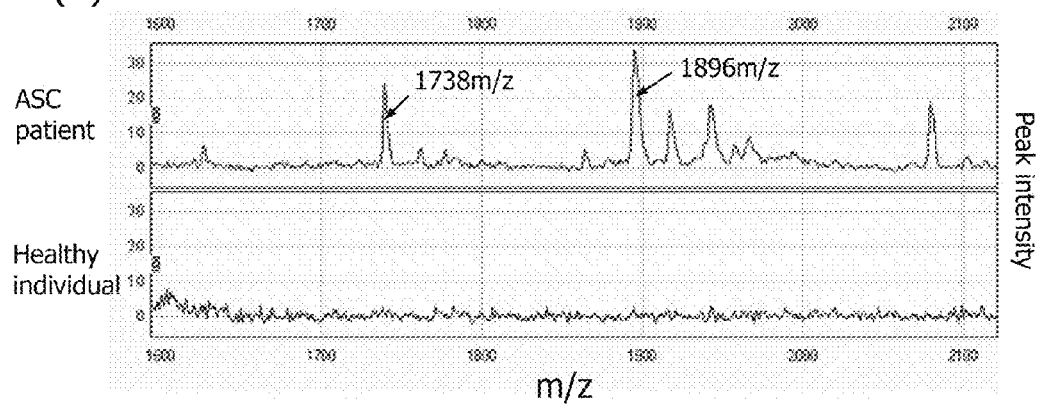
Figure 16:
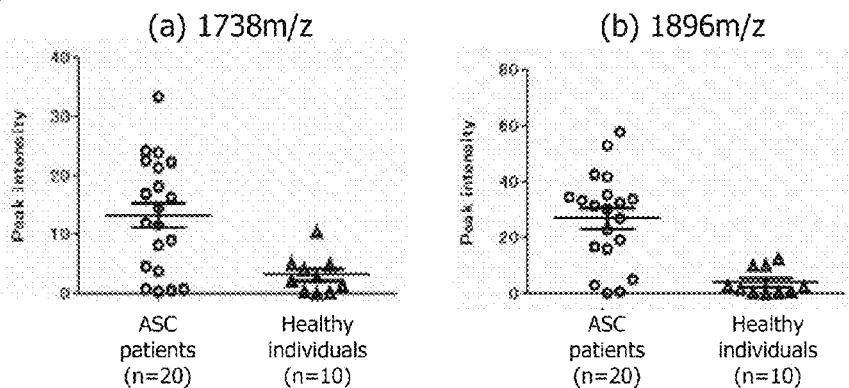

According to the present invention, as shown in FIG. 16, healthy individuals may be first discriminated from patients with NAFLD using the kininogen-based marker, and then, patients with chronic hepatitis may be conveniently discriminated from ASCs in the patients with NAFLD by combining the C4-based markers. In particular, progress of chronic hepatitis may be conveniently determined, resulting in planning of an appropriate treatment in an early stage.

EXAMPLES

Example 1

Kininogen

[1] Detection Serum Peptide by ClinProt System
(1) Material and Method

As serum samples, sera of 44 patients with NAFLD and 24 healthy individuals were used. Five microliters of each serum were added to WCX beads for adsorbing the peptides of serum proteins on the WCX beads. Unadsorbed peptides were removed by washing, and then the peptides adsorbed on the WCX beads were eluted by an elution solution.

Then, crystals of the peptides and a matrix were prepared. In the preparation, 1 mg of CCA was added to 1 mL of acetone, and 300 μL of the mixture and 600 μL of ethanol were well mixed. Then, 2 μL of the ClinProt eluate was mixed with 18 μL of the prepared CCA solution. One microliter of the resulting mixture was placed dropwise on a thin film, followed by air drying to crystallize the peptides and CCA.

The peaks were detected by the linear mode measurement of Autoflex to obtain a mass spectrum. The mass spectrum of a healthy individual was compared with that of a patient with NAFLD using a ClinPro tool (Bruker Daltonics), and the peaks increased in the patient with NAFLD were selected as candidates of NAFLD markers. Diagnostic marker candidates were screened in a mass range of 3000 m/z or less. In comparison of a plurality of mass spectra, peaks having m/z values that were in agreement with each other within an error of 0.2% were recognized as being derived from the same molecule. The significant difference between the NAFLD patient group and the healthy individual group was investigated by Student's t-test, and peaks of P<0.05 were determined to be significant.

(2) Results

Peaks (P<0.05) that significantly increased in the NAFLD patient group were further determined from the spectra of the NAFLD patient group and the healthy individual group, and peaks having an intensity of 50 or more were selected. Table 1 shows a list of the peaks. FIG. 3(A) shows typical spectral patterns of a patient with NAFLD and a healthy individual. In these peaks, the peaks at 1942 m/z, 2079 m/z, and 2207 m/z (FIG. 3(B)) had particularly high intensities compared to other peaks (Table 1).

TABLE 1

| Peaks increased in expression in patients with NAFLD (ClinProt) | | | |
|---|---|---|---|
| m/z | Patient with NAFLD (n = 44) Peak intensity | Healthy individual (n = 24) Peak intensity | P value |
| 1942.88 | 435.01 ± 213.79 | 45.44 ± 71.52 | 2.61 × 10<sup>−14</sup> |
| 2079.79 | 334.72 ± 187.24 | 69.65 ± 115.17 | 9.57 × 10<sup>−9</sup> |
| 2207.68 | 158.52 ± 96.78 | 63.05 ± 143.36 | 0.0154 |
| 2858.61 | 151.37 ± 82.25 | 77.01 ± 49.46 | 6.92 × 10<sup>−5</sup> |

TABLE 1-continued

| Peaks increased in expression in patients with NAFLD (ClinProt) | | | |
|---|---|---|---|
| m/z | Patient with NAFLD (n = 44) Peak intensity | Healthy individual (n = 24) Peak intensity | P value |
| 2928.29 | 83.05 ± 42.66 | 59.67 ± 21.07 | 0.00854 |
| 2986.07 | 56.58 ± 50.66 | 24.07 ± 18.35 | 0.000823 |

* data shows average ± standard deviation

The plot of the intensities of these three peaks of each sample shows remarkably high values in patients with NAFLD as shown by (a), (b), and (c) in FIG. 3(C). Then, the cut-off value for diagnosis was set to [(average peak intensity of healthy individuals)+2×(standard deviation)]. A specimen with a value not lower than the cut-off value was determined to be NAFLD, and a specimen with a value lower than the value was determined to be a healthy individual, and 44 patients with NAFLD and 24 healthy individuals were subjected to diagnosis. First, in diagnosis using the peak at 1942 m/z, 40 subjects among the 44 NAFLD subjects were diagnosed as NAFLD (sensitivity: 90.9%), and 20 subjects among the 24 healthy individual subjects were diagnosed as healthy individuals (specificity: 87.5%). In diagnosis using the peak at 2079 m/z, the NAFLD diagnosis showed a sensitivity of 72.7% and a specificity of 87.5%. Furthermore, in the peak at 2207 m/z, the NAFLD diagnosis showed a sensitivity of 70.5% and a specificity of 91.7%. Based on these results, the peaks at 1942 m/z, 2079 m/z, and 2207 m/z were determined as candidates of NAFLD markers, and peptides come from these peaks were identified.

[2] Identification of Kininogen as NAFLD Marker

In order to identify the peptides come from the peaks at 1942 m/z, 2079 m/z, and 2207 m/z, MS/MS ion search was performed. The detail will be described below.

(1) Material and Method

An MS/MS spectrum was acquired as follows: First, crystals of the peptides and a matrix were prepared by a thin film technique. A saturated aceton solution of CCA was applied to the anchor surface of an anchor chip in advance to form a thin film of CCA. Then, 1 μL of ClinProt eluate of an NAFLD patient serum was placed dropwise on the thin film, followed by leaving to stand for about 5 minutes to crystallize the peptides in the eluate and CCA. Then, the crystal was washed with 3 μL of a 0.1% TFA three times.

The molecular weight of the target peak was measured with high accuracy in the reflector mode of Autoflex. The MS/MS spectrum was acquired by lift mode measurement for obtaining the molecular weights of the target peak (parent ions) and their fragments (ions of partial peptides). The molecular weight was corrected (calibrated) by peptide calibration standard 2 (Bruker Daltonics). Based on the observed MS/MS spectrum, a peak list of the parent ions and their fragment ions was made using BioTools (Bruker Daltonics), and the peaks were identified by MS/MS ion search of Mascot search (Matrix Science). In the identification, the database of SwissProt was used.

(2) Results

Figure 4:
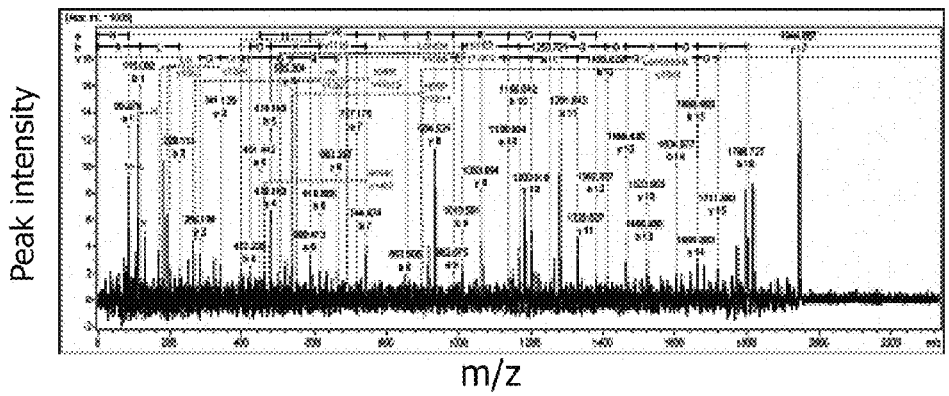
FIG. 4 includes graphs showing MS/MS spectra of marker candidate peptides at 1942 m/z Graph (A), 2079 m/z Graph (B), and 2207 m/z Graph (C).
Figure 4:
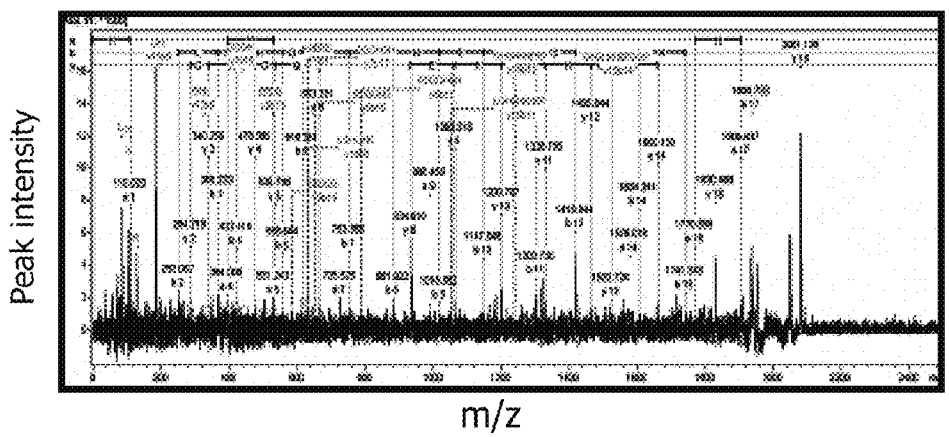
Figure 4:
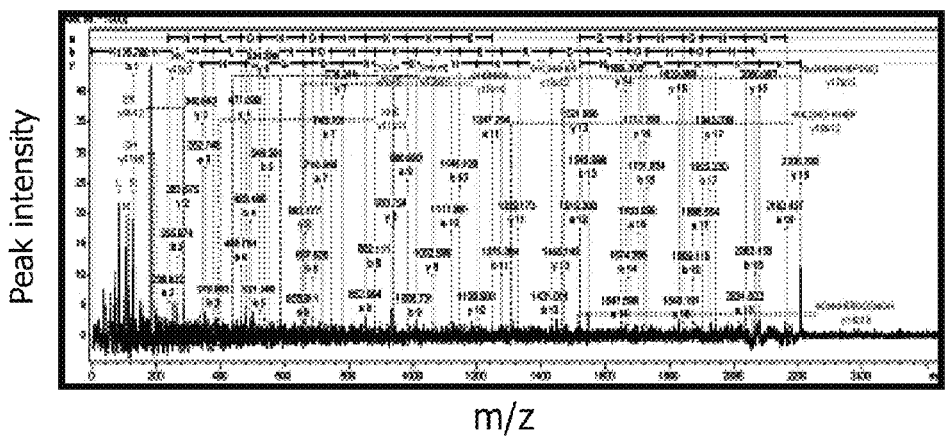

FIG. 4 shows MS/MS spectra at 1942 m/z (A), 2079 m/z (B), and 2207 m/z (C). Screening of all the peptides that agree with peak information of these spectra revealed that all of the three peaks were parts of a high-molecular-weight kininogen. Table 2 shows Accession Numbers and peptide sequences of the high-molecular-weight kininogen.

TABLE 2

Identification of NAFLD marker by MS/MS ion search

| m/z | Results of identification | Accession No. (SwissProt) | Sequence |
|---|---|---|---|
| 1942 | Kininogen-1 precursor | P01042 | Asn Leu Gly His Gly His Lys His Glu Arg Asp Gln Gly His Gly His Gln |
| 2079 | Kininogen-1 precursor | P01042 | His Asn Leu Gly His Gly His Lys His Glu Arg Asp Gln Gly His Gly His Gln |
| 2207 | Kininogen-1 precursor | P01042 | Lys His Asn Leu Gly His Gly His Lys His Glu Arg Asp Gln Gly His Gly His Gln |

The results demonstrate that any of the peptides belongs to domain 5 of the high-molecular-weight kininogen and that 1942 m/z, 2079 m/z, and 2207 m/z correspond to 440th to 456th, 439th to 456th, and 438th to 456th amino acid sequences, respectively.

[3] Decomposition of Full-Length Kininogen in NAFLD Patient Serum

The identified peptides are parts of domain 5 of the high-molecular-weight kininogen. The molecular weight of the full-length kininogen protein is about 120 kDa. The identified three peaks, which are parts of the full length, suggest a possibility of facilitated decomposition of the kininogen by the onset of NAFLD. The relationship between NAFLD and the kininogen has not been known yet. Consequently, the decomposition of the full-length kininogen was investigated in patients with NAFLD by Western blotting using an anti-kininogen antibody.

(1) Material and Method (Polyclonal Antibody)

A sample for electrophoresis was prepared as follows. After 5 μL of a serum of a patient with NAFLD or a healthy individual was mixed with 45 μL of PBS, 400 μL of acetone was added thereto. The mixture was left at −80° C. overnight for acetone precipitation of serum proteins. The precipitated proteins were collected by centrifugation and were dissolved in an electrophoresis sample buffer, followed by treatment at 100° C. for 5 minutes. The completely denatured and reduced proteins were subjected to SDS-PAGE on 8% acrylamide gel for separating the proteins. The separated proteins were transferred to a PVDF membrane. After being blocked with 5% skim milk/0.05% Tween 20/PBS, the proteins were reacted for 1 hour with RABBIT ANTI HUMAN HMW-KININOGEN Catalog Number 5575-4957 (manufactured by AbD Serotec) for the full-length kininogen and rabbit-anti-human-kininogen (Sigma-Aldrich Japan contract product), which is specific to K438-Q456 peptides, as an antibody specifically recognizing the identified partial peptide C. After treatment with an HRP-labeled secondary antibody, specific bands were detected with ECL Western Blotting Detection System (GE Healthcare).

(2) Results

Figure 5:
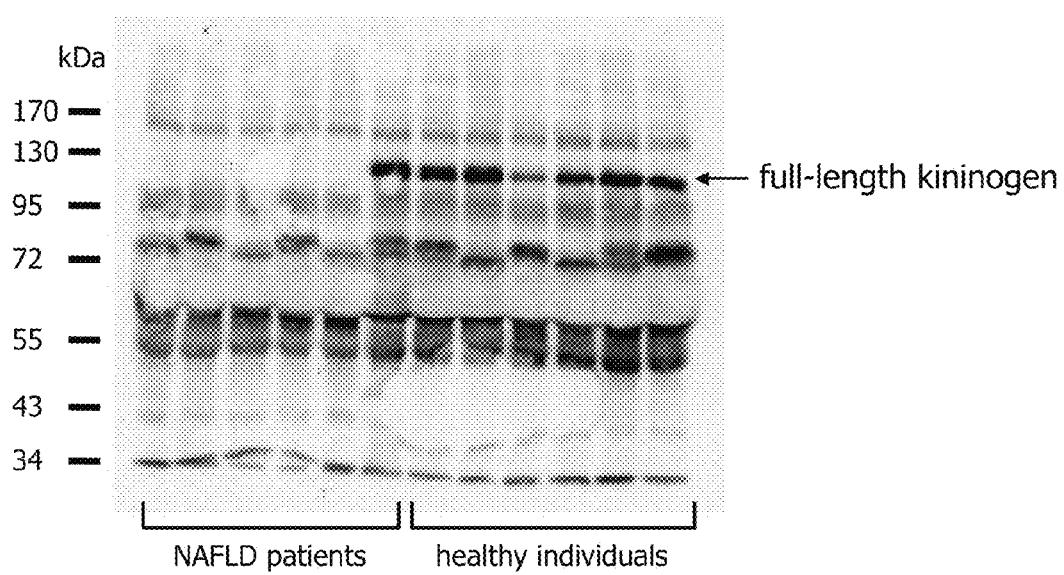
FIG. 5 is a photograph showing the results of Western blotting using RABBIT ANTI HUMAN HMW-KININOGEN (anti-kininogen polyclonal antibody) manufactured by AbD Serotec.
Figure 6:
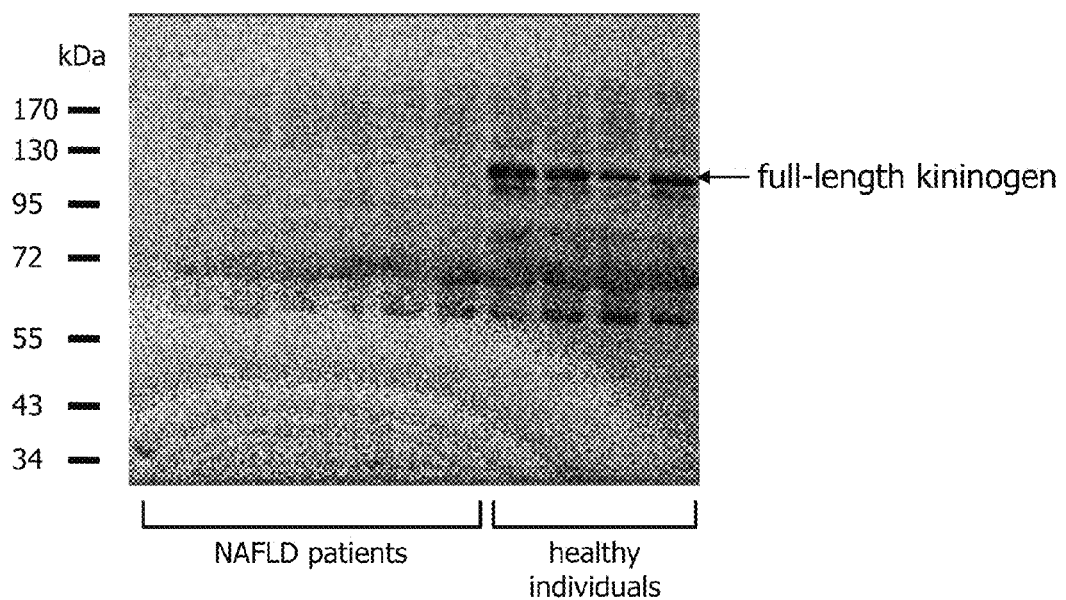
FIG. 6 is a photograph showing the results of Western blotting using Rabbit-antihuman-kininogen (anti-kininogen polyclonal antibody) manufactured by Sigma-Aldrich Japan.

FIG. 5 shows the results of Western blotting using an anti-kininogen polyclonal antibody (the above-mentioned RABBIT ANTI HUMAN HMW-KININOGEN manufactured by AbD Serotec). In 18 subjects among the 19 healthy individual subjects, the full-length high-molecular-weight kininogen of about 120 kDa was detected, and a band of the high-molecular-weight kininogen heavy chain of about 65 kDa and a band of the light chain of about 45 kDa were also detected. On the other hand, in patients with NAFLD, the band of the full-length high-molecular-weight kininogen was not detected in 36 subjects among the 37 subjects. Similarly, FIG. 6 shows the results of the rabbit-anti-human-kininogen (Sigma-Aldrich Japan contract product), which specifically recognizes the identified peptide. In the healthy individuals, the full-length high-molecular-weight kininogen of about 120 kDa was detected in all of four subjects. In the patients with NAFLD, the band of the full-length high-molecular-weight kininogen was not detected in all of eight subjects. These results reveal that the full-length high-molecular-weight kininogen decreases in the patients with NAFLD.

(3) Material and Method (Monoclonal Antibody)

A sample for electrophoresis was prepared as follows. After 5 μL of a serum of a patient with NAFLD or a healthy individual was mixed with 45 μL of PBS, 400 μL of acetone was added thereto. The mixture was left at −80° C. overnight for acetone precipitation of serum proteins. The precipitated proteins were collected by centrifugation and were dissolved in an electrophoresis sample buffer, followed by treatment at 100° C. for 5 minutes. The completely denatured and reduced proteins were subjected to SDS-PAGE on 8% acrylamide gel for separating the proteins. The separated proteins were transferred to a PVDF membrane. After being blocked with 5% skim milk/0.05% Tween 20/PBS, the proteins were reacted with an anti-kininogen monoclonal antibody. The anti-kininogen antibody used was, (mouse-monoclonal) HMW Kininogen Light Chain antibody [1.B.709]: Catalog Number: GTX14514 (manufactured by GeneTex Inc.). The anti-kininogen monoclonal antibody specifically recognizing a portion containing the identified peptide C used was (mouse-monoclonal) Anti-human-kininogen/Kininostatin Antibody: Catalog Number: MAB1569 (manufactured by R&D Systems), which is specific to K438-5531 peptides. The reaction with the antibody was performed for 1 hour. After treatment with an HRP-labeled secondary antibody, specific bands were detected with ECL Western Blotting Detection System (GE Healthcare).

(4) Results

Figure 7:
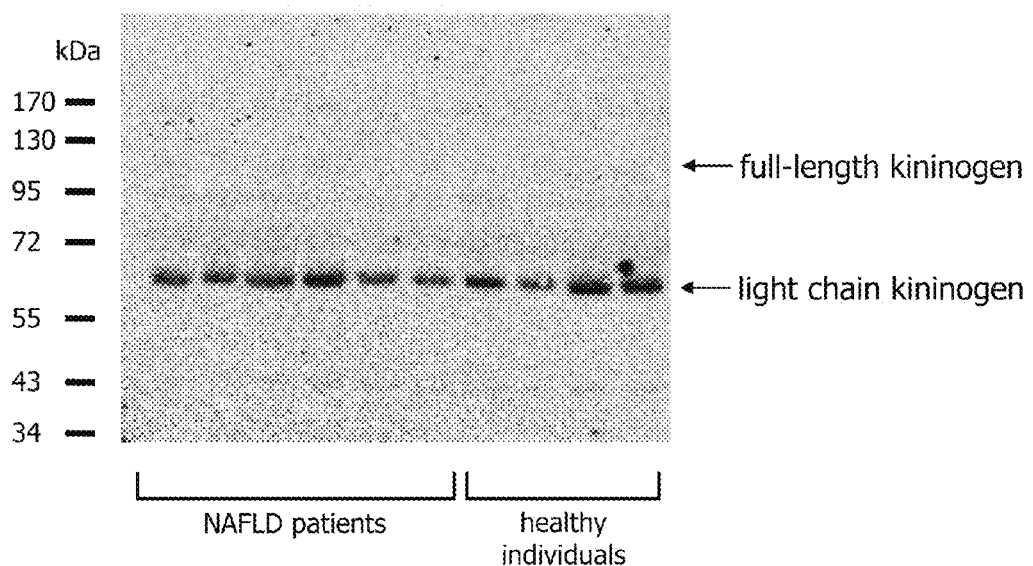
FIG. 7 is a photograph showing the results of Western blotting using HMW Kininogen Light Chain antibody [1.B.709] (anti-kininogen monoclonal antibody) manufactured by GeneTex.
Figure 8:
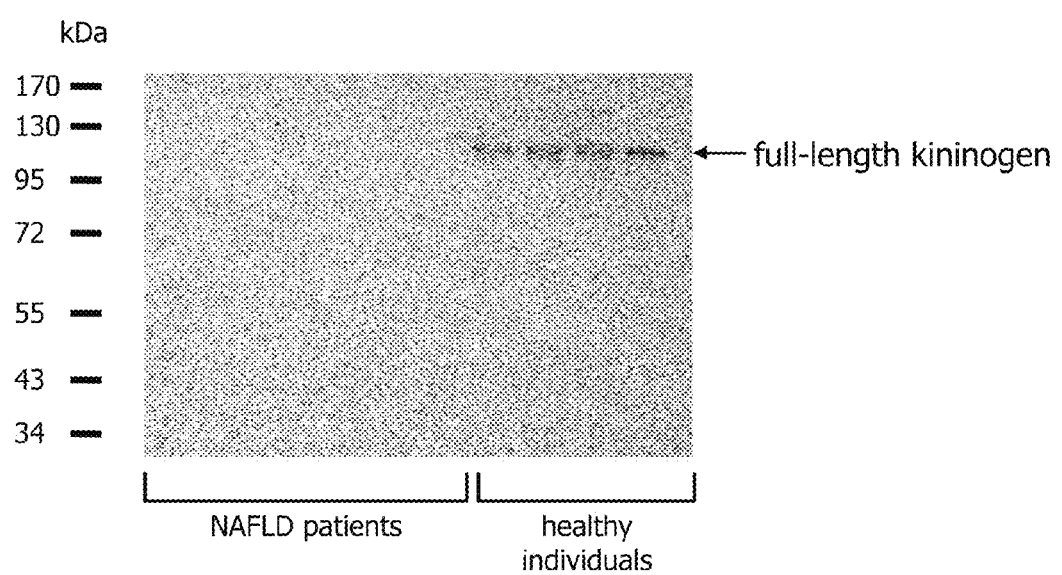
FIG. 8 is a photograph showing the results of Western blotting using Anti-human-kininogen/Kininostatin Antibody (anti-kininogen polyclonal antibody) manufactured by R&D Systems.

FIG. 7 shows the results of Western blotting using the anti-kininogen monoclonal antibody (the above-mentioned HMW Kininogen Light Chain antibody [1.B.709] manufactured by GeneTex Inc.). The band of the light chain of about 45 kDa was detected, but a significant difference was not found between the healthy individuals and patients with NAFLD. FIG. 8 shows the results of anti-kininogen monoclonal antibody (the above-mentioned Anti-human-kininogen/Kininostatin Antibody manufactured by R&D Systems), which specifically recognizes the portion containing the identified partial peptide C. In the healthy individuals, the full-length high-molecular-weight kininogen of about 120 kDa was detected in 15 subjects among the 16 subjects. In the patients with NAFLD, the band of the full-length high-molecular-weight kininogen was not detected in 36 subjects among the 40 subjects. These results reveal that the full-length high-molecular-weight kininogen decreases in patients with NAFLD.

[5] Detection of Kininogen Peptide with Anti-Kininogen Antibody

In order to use these markers for diagnosis, it is necessary to detect specific peaks using antibodies against the markers. Accordingly, the inventors tried to detect the kininogen by immunoprecipitation using an anti-kininogen antibody.

(1) Material and Method

The specific detection of kininogen partial peptides was performed by immunoprecipitation using anti-kininogen antibodies. Ten microliters of an NAFLD patient serum was mixed with 40 µL of PBS, followed by addition of 10 µL of RABBIT ANTI HUMAN HMW-KININOGEN (manufactured by AbD Serotec) or rabbit-anti-human-kininogen (Sigma-Aldrich Japan contract product) as the polyclonal antibody or HMW Kininogen Light Chain antibody [1.B.709] (manufactured by GeneTex Inc.) or Anti-human-kininogen/Kininostatin Antibody: Catalog Number: MAB1569 (manufactured by R&D Systems) as the monoclonal antibody. The mixture was left to stand on ice bath (4° C.) for 1 hour for a reaction of the antigen in the serum and the antibody. After 30 µL of 50% protein A sepharose beads were added thereto, the mixture was left to stand on an ice bath for 1 hour while being inverted for mixing every 10 minutes. Then, the mixture was separated by centrifugation into a precipitate and a supernatant. The precipitated beads were washed five times with 400 µL of PBS to remove unadsorbed proteins and peptides, and the proteins and peptides adsorbed onto the beads were eluted by addition of 30 µL of 50% acetonitrile and centrifugation. Twenty microliters of the eluate was diluted with 80 µL of 50 mM sodium acetate (pH 4.5), followed by application to CM10 by shaking treatment for 30 minutes. The spots were washed and air-dried, followed by addition of 0.5 µL of 20% saturated CCA/50% acetonitrile/0.5% TFA twice. The identified kininogen partial peptides were detected by SELDI measurement.

(2) Results

Figure 9:
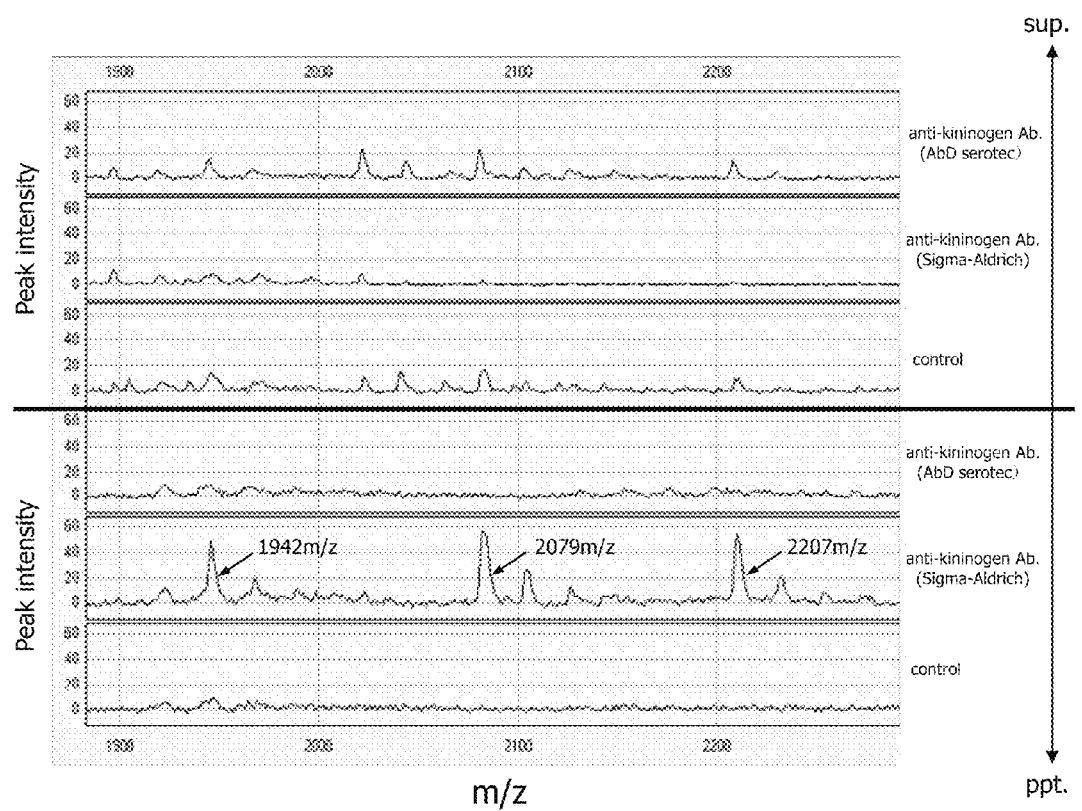
FIG. 9 is a graph showing the results of measurement of 1942 m/z (a), 2079 m/z (b), and 2207 m/z (c) peaks by immunoprecipitation using anti-kininogen polyclonal antibodies (an AbD Serotec product and a Sigma-Aldrich contract product), the vertical axis represents peak intensity, and the horizontal axis represents molecular weight.

FIG. 9 shows the results of immunoprecipitation with polyclonal antibodies. The peak intensities of NAFLD patient sera treated with the rabbit-anti-human-kininogen manufactured by Sigma-Aldrich Japan were higher than those treated with RABBIT ANTI HUMAN HMW-KININOGEN manufactured by AbD Serotec.

Figure 10:
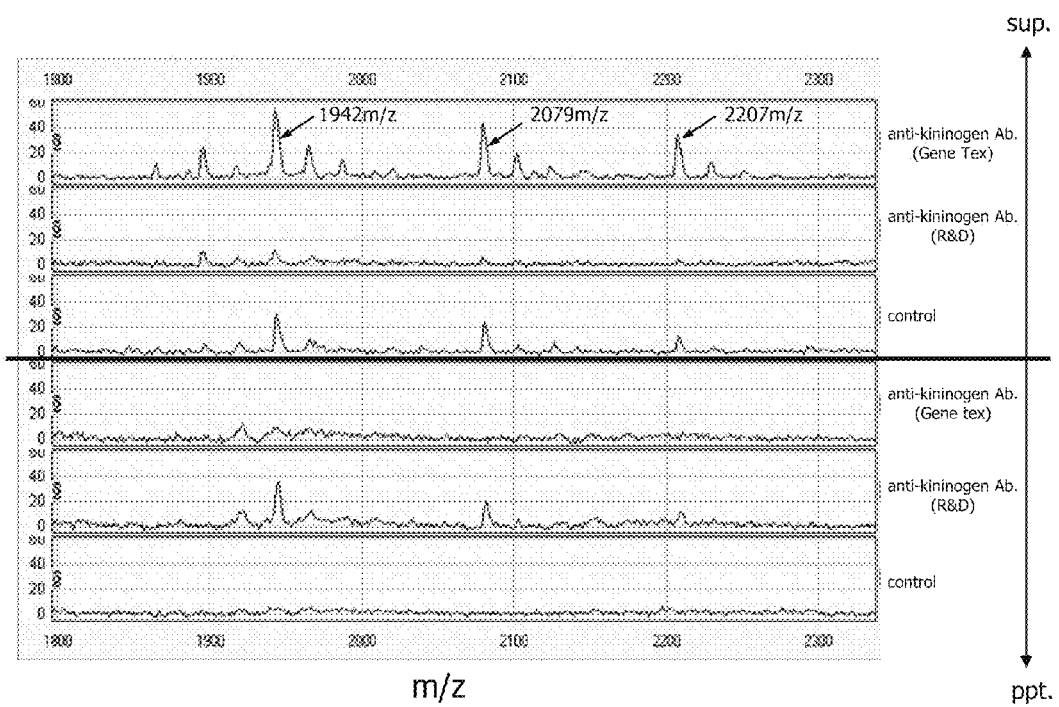
FIG. 10 is a graph showing the results of measurement of 1942 m/z (a), 2079 m/z (b), and 2207 m/z (c) peaks by immunoprecipitation using anti-kininogen monoclonal antibodies (products of GeneTex and R&D Systems), the vertical axis represents peak intensity, and the horizontal axis represents molecular weight.

Similarly, FIG. 10 shows the results of immunoprecipitation with monoclonal antibodies. The peak intensities of sera treated with the Anti-human-kininogen/Kininostatin Antibody manufactured by R&D Systems are higher than those treated with the HMW Kininogen Light Chain antibody [1.B.709] manufactured by GeneTex. That is, antibodies specifically recognizing the identified portion more remarkably react with the identified kininogen peptide portion.

[6] Detection of Kininogen-Derived Peak Using Protein Chip System (SELDI)

A protein chip system (Bio-Rad) consists of a protein chip and SELDI and is useful for screening serum diagnostic markers as in ClinProt. The chip surface is labeled with various functional groups and captures proteins and peptides in a serum applied thereto. Peaks are detected by measurement with the SELDI. The inventors then tried to investigate whether partial peptide peaks (1942 m/z, 2079 m/z, and 2207 m/z) derived from the kininogen are also detected by the protein chip system.

(1) Material and Method

The serum was applied to the protein chip as follows. Five microliters of the serum were added to 45 µL of a urea buffer (7 M urea, 2 M thiourea, 4% CHAPS, 1% DTT, and 2% Ampholyte). The mixture was left to stand on an ice bath for 10 minutes to denature the serum proteins and then diluted with 450 µL of 50 mM sodium acetate having a pH of 4.5, followed by centrifugation at 10000 rpm for 5 minutes with being cooled (4° C.). The supernatant was transferred to a tube and stored on an ice bath. One hundred microliters of the diluted supernatant were added to a cation exchange chip CM10 (Bio-Rad) equilibrated in advance. After osmotic treatment at room temperature for 30 minutes, the CM10 was washed with 100 µL of 50 mM sodium acetate at a pH of 4.5 three times and then with ultrapure water twice. After air drying, 0.5 µL of a 50% saturated CCA were added to the spot twice to prepare a crystal mixture of the peptides and CCA. The peaks were detected with SELDI.

The peak intensities of the NAFLD patient group and the healthy individual group were investigated with marker Wizard software (Bio-Rad). In comparison of a plurality of mass spectra, peaks having m/z values that were in agreement with each other within an error of 0.3% were recognized as being derived from the same molecule. The significant difference between these groups was determined by a Mann-Whitney U test, and a peak was determined to be significant at P<0.05.

(2) Results

Figure 11:
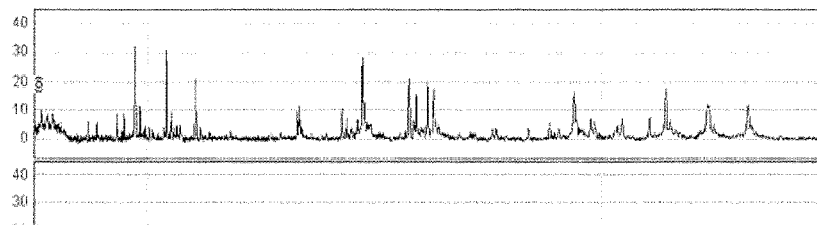
FIG. 11 includes graphs showing spectral comparison of patients with NAFLD and healthy individuals using a protein chip; Graph (A) shows typical spectral patterns of a patient with NAFLD and a healthy individual measured by SELDI; Graph (B) shows an enlarged view of a region near 1800 to 2300 m/z in Graph (A), and three peaks observed in the patient with NAFLD are peaks at 1942 m/z, 2079 m/z, and 2207 m/z from the left; and Graph (C) plots peak intensities of the patients with NAFLD and the healthy individuals at 1942 m/z (a), 2079 m/z (b), and 2207 m/z (c).
Figure 11:
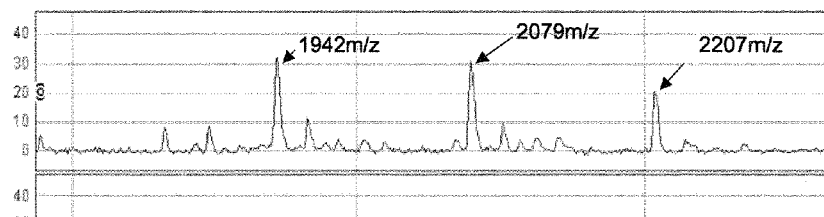
Figure 11:
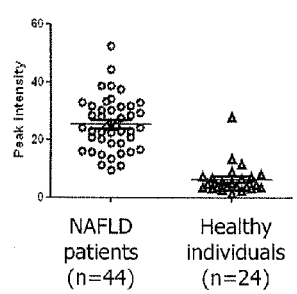
Figure 11:
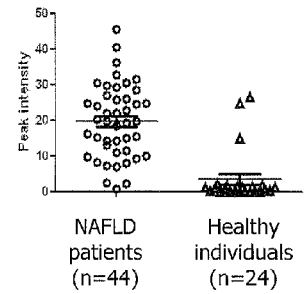
Figure 11:
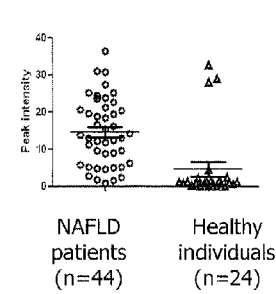

Peaks (P<0.05) that significantly increases in the NAFLD patient group were further selected from the spectra of the NAFLD patient group and the healthy individual group, and peaks having an intensity of 5 or more were selected. Table 3 shows a list of the peaks. FIG. 11(A) shows typical spectral patterns of a patient with NAFLD and a healthy individual. Like Example 1, the results reveal that the peaks at 1942 m/z, 2079 m/z, and 2207 m/z (FIG. 11(B)) derived from the high-molecular-weight kininogen are significantly higher in patients with NAFLD compared to those in healthy individuals (Table 3). The peak intensities plotted for each sample are also remarkably high in patients with NAFLD (FIG. 11(C)).

TABLE 3

Peaks with increased expression in patient with NAFLD (Protein chip)

| m/z | Patient with NAFLD (n = 44) Peak intensity | Healthy individual (n = 24) Peak intensity | P value |
| --- | --- | --- | --- |
| 1942 | 25.57 ± 9.13 | 6.74 ± 5.40 | $2.0 \times 10^{-10}$ |
| 1965 | 10.57 ± 3.79 | 4.98 ± 2.28 | $2.4 \times 10^{-8}$ |
| 2019 | 10.70 ± 10.23 | 2.34 ± 2.38 | $3.6 \times 10^{-5}$ |
| 2079 | 19.75 ± 10.34 | 3.42 ± 7.48 | $1.9 \times 10^{-8}$ |
| 2207 | 14.63 ± 9.02 | 4.65 ± 9.81 | $1.0 \times 10^{-6}$ |
| 2656 | 8.49 ± 4.04 | 5.72 ± 6.89 | 0.00112 |
| 2858 | 7.04 ± 4.35 | 2.27 ± 2.99 | $1.2 \times 10^{-6}$ |
| 2949 | 24.58 ± 9.80 | 13.78 ± 8.0 2 | $5.0 \times 10^{-5}$ |

Example 2

Complement C4

[1] Detection of Serum Peptide with ClinProt System (1) Material and Method

As serum specimens, sera of 19 ASCs and 24 healthy individuals were used. Five microliters of each serum was added to WCX beads for adsorbing the peptides of serum proteins to the WCX beads. Unadsorbed peptides were washed out, and then the peptides adsorbed to the WCX beads were eluted by adding an elution solution.

Then, crystals of the peptides and a matrix were prepared. In the preparation, 1 mg of CCA was added to 1 mL of acetone, and 300 μL of the mixture and 600 μL of ethanol were well mixed to each other. Then, 2 μL of the ClinProt eluate was mixed with 18 μL of the prepared CCA solution. One microliter of the resulting mixture was placed dropwise on a thin film, followed by air drying to crystallize the peptides and CCA.

The peaks were detected by the linear mode measurement of Autoflex to obtain a mass spectrum. The mass spectra of a healthy individual and ASC were compared with each other using a ClinPro tool (Bruker Daltonics), and the peaks increasing in the ASC were determined as candidates of ASC markers. Candidates of diagnostic markers were screened in a mass range of 3000 m/z or less. In comparison of a plurality of mass spectra, peaks having m/z values that were in agreement with each other within an error of 0.2% were recognized as being derived from the same molecule. The significant difference between the ASC group and the healthy individual group was investigated by Student's t-test, and peaks were determined to be significant at P<0.05.

(2) Result

Figure 12:
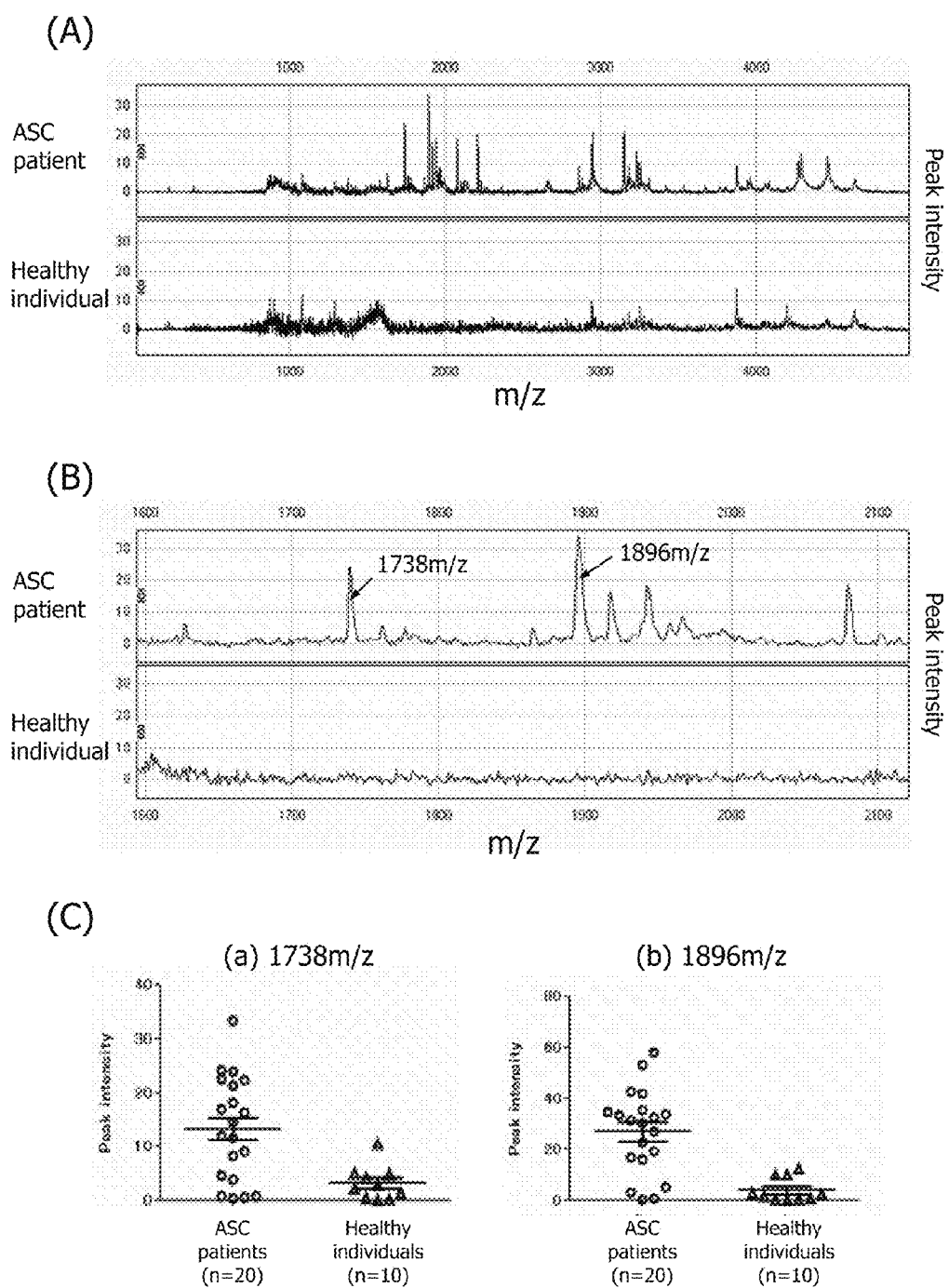
FIG. 12 includes graphs showing spectral comparison of ASCs and healthy individuals using ClinProt; Graph (A) shows typical spectral patterns of an ASC and a healthy individual measured by a linear mode of Autoflex; Graph (B) shows an enlarged view of the region near 1600 to 2000 m/z in Graph (A), and two peaks observed in the ASC are peaks at 1738 m/z and 1896 m/z from the left; the vertical axis represents peak intensity; and Graph (C) plots peak intensities of the ASCs and the healthy individuals at 1738 m/z (a) and 1896 m/z (b).

Significantly increasing peaks (P<0.05) were detected from the spectra of the ASC group and the healthy individual group, and peaks having an intensity of 50 or more were selected. Table 4 shows a list of the peaks, and FIG. 12(A) shows typical spectral patterns of ASC and a healthy individual. In these peaks, the peaks at 1738 m/z and 1896 m/z (FIG. 12(B)) have higher peak intensities compared to other peaks (Table 4).

TABLE 4

Peaks with increasing expression in asymptomatic carrier (ClinProt)

| m/z | ASC (n = 44) Peak intensity | Healthy individual (n = 24) Peak intensity | P value |
| --- | --- | --- | --- |
| 1497.98 | 15.76 ± 12.8 | 4.66 ± 2.92 | $6.1 \times 10^{-5}$ |
| 1738.06 | 100.88 ± 63.16 | 57.79 ± 44.48 | 0.00971 |
| 1777.32 | 26.12 ± 15.93 | 16.27 ± 13.49 | 0.0286 |
| 1864.04 | 50.84 ± 35.4 | 21.35 ± 21.11 | $7.2 \times 10^{-4}$ |
| 1895.98 | 94.68 ± 58.7 | 31.63 ± 21.1 | $4.0 \times 10^{-6}$ |
| 1942.69 | 180.35 ± 137.12 | 39.8 ± 41.5 | $6.3 \times 10^{-6}$ |
| 2079.63 | 162.02 ± 62.26 | 56.33 ± 67.19 | $4.0 \times 10^{-6}$ |
| 2207.47 | 124.1 ± 70.24 | 46.93 ± 89.11 | 0.0041 |

* data shows average ± standard deviation

These two peaks obviously exhibit remarkably high values in ASC (FIG. 12(C)) in the plot of the peak intensities for each sample. Then, the cut-off value for diagnosis was set to [(average peak intensity of healthy individuals)+2×(standard deviation)]. A specimen with a value not lower than the cut-off value was determined to be an ASC, and a specimen with a value lower than the value was determined to be a healthy individual, and 19 ASC subjects and 24 healthy individuals were subjected to diagnosis.

First, in diagnosis using the peak at 1738 m/z, 15 subjects among the 19 ASC subjects were diagnosed as ASC (sensitivity: 78.9%), and 21 subjects among the 24 healthy individuals were diagnosed as healthy individuals (specificity: 87.5%). The diagnostic results at the peak at 1896 m/z were similar to the above. Based on these results, the peaks at 1738 m/z and 1896 m/z were determined as candidates of ASC markers, and peptides come from these peaks were identified.

[2] Identification of Sequences D and E as Liver Disease Marker

In order to identify peptides come from the peaks at 1738 m/z and 1896 m/z, MS/MS ion search was performed. The detail will be described below.

(1) Material and Method

An MS/MS spectrum was acquired as follows. First, crystals of the peptides and a matrix were prepared by a thin film technique. A saturated aceton solution of CCA was applied to the anchor surface of an anchor chip in advance to form a thin film of CCA. Then, 1 μL of ClinProt eluate of an ASC serum was placed dropwise on the thin film, followed by leaving to stand for about 5 minutes to crystallize the peptides in the eluate and CCA. Then, the crystal was washed three times with 3 μL of 0.1% TFA.

The molecular weight of a target peak was measured with high accuracy in the reflector mode of Autoflex. The MS/MS spectrum was acquired by lift mode measurement for obtaining the molecular weights of a target peak (parent ions) and their fragments (ions of partial peptides). The molecular weight was corrected (calibrated) by peptide calibration standard 2 (Bruker Daltonics). Based on the observed MS/MS spectrum, a peak list of the parent ions and the partial peptide sequence ions was made using BioTools (Bruker Daltonics), and the peaks were identified by MS/MS ion search of Mascot search (Matrix Science). The identification was performed using database of SwissProt.

(2) Results

Figure 13:
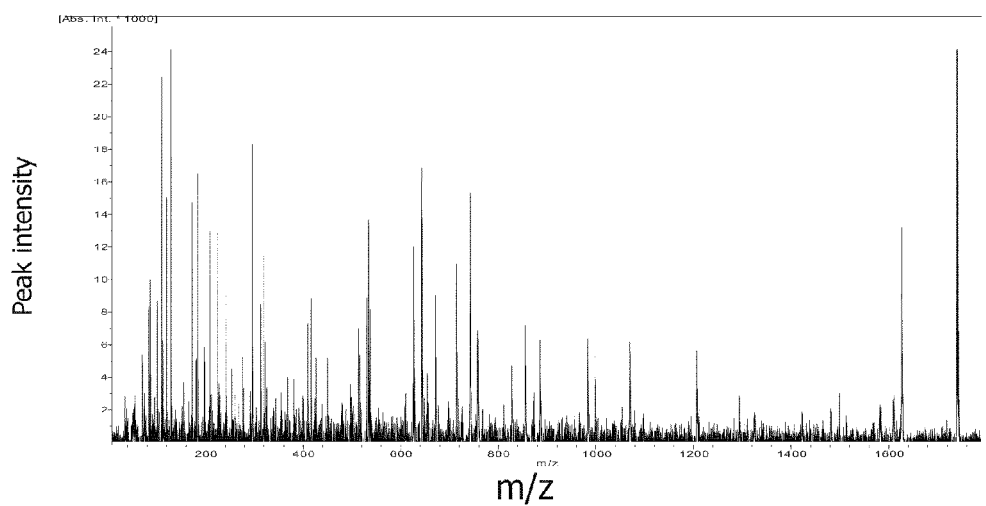
FIG. 13 includes graphs showing MS/MS spectra of marker candidate peptides identified in ASCs using a database of SwissProt at 1738 m/z (A) and 1896 m/z (B).

FIG. 13 shows MS/MS spectra at 1738 m/z (A) and 1896 m/z (B). The peptides that agree with peak information of these spectra were screened to confirm that both the two peaks were decomposition products of C4. Table 5 shows the sequences of the peptides.

TABLE 5

Identification of ASC marker by MS/MS ion search

| m/z | Results of identification | Accession No. (SwissProt) | Sequence |
| --- | --- | --- | --- |
| 1738 | Complement C4-A precursor (Complement C4-B precursor) | POCOL4 (POCOL5) | Asn Gly Phe Lys Ser His Ala Leu Gln Leu Asn Asn Arg Gln Ile |
| 1896 | Complement C4-A precursor (Complement C4-B precursor) | POCOL4 (POCOL5) | Asn Gly Phe Lys Ser His Ala Leu Gln Leu Asn Asn Arg Gln Ile Arg |

The results show that the 1738 m/z and 1896 m/z correspond to 1337th to 1351st and 1337th to 1352nd amino acid sequences, respectively.

Figure 14:
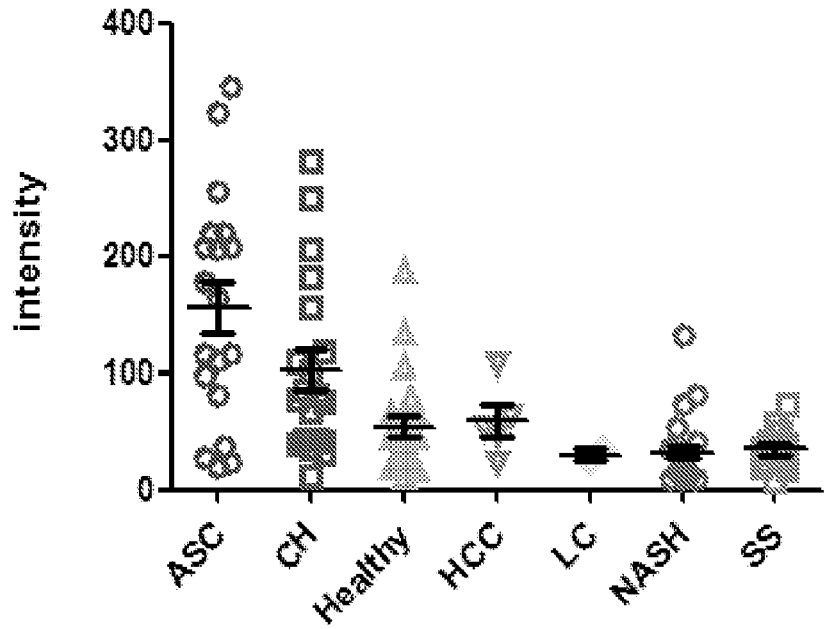
FIG. 14 includes the results of analysis of peaks at 1738 m/z (a) and 1896 m/z (b) using a ClinProt system.
Figure 14:
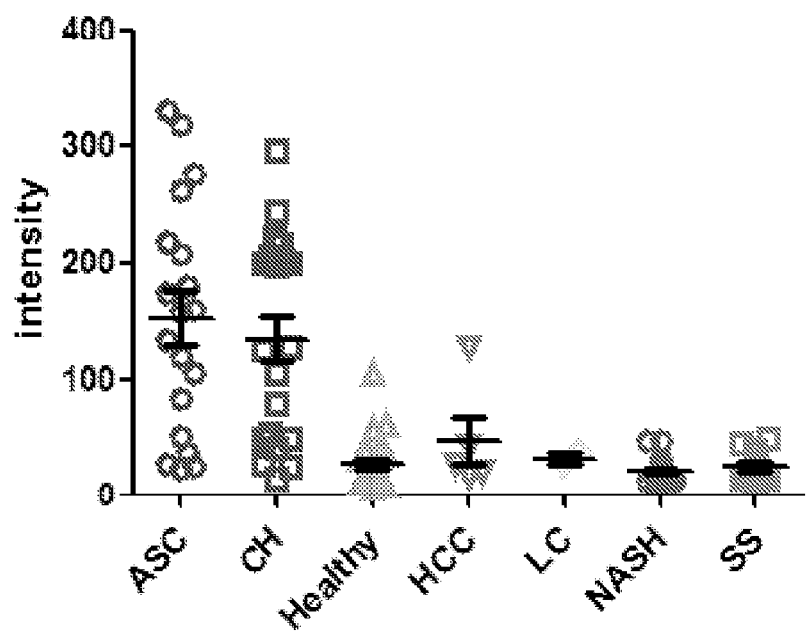

The peaks at 1738 and 1896 m/z were analyzed with the ClinProt system. Specimens were sera of 30 ASC subjects, 30 patients with chronic hepatitis (CH), 2 patients with liver cirrhosis (LC), 5 patients with hepatocellular carcinoma (HCC), 12 SS subjects, 25 NASH subjects, and 25 healthy individuals. FIG. 14 shows the results. A significant difference was uncertain between ASC and chronic hepatitis (CH), but a significant difference was found between these subjects and healthy individuals or other disease subjects.

[3] Detection of Serum Protein Level by ELISA

It is publicly known that the complement system is activated in hepatocellular carcinoma and liver cirrhosis. However, a novel marker of an early stage liver disease may be found out by quantitative determination of a factor specific to C4a or an activating path on ASC or NAFLD (SS and NASH), which are relatively early stage liver diseases. Such finding fits to the purpose of the present invention to provide a larger number of markers of (early) liver diseases. Accordingly, quantitative determination of a factor serving as an index of activation of C4a was tried in such carriers and liver disease patients.

(1) Material and Method

The serum level of C4a was measured with a C4a enzyme immunoassay BD OptEIA Set (Becton Dickinson Japan, hereinafter abbreviated to BD). Specimens were sera of 30 ASC subjects, 30 patients with chronic hepatitis (CH), 2 patients with liver cirrhosis (LC), 5 patients with hepatocellular carcinoma (HCC), 12 SS subjects, 25 NASH subjects, and 25 healthy individuals. A C4a monoclonal antibody is immobilized to each well of the 96-well plate of this kit.

Two microliters of each serum was diluted with 600 µL of PBS (137 mM NaCl, 8.1 mM $Na_2HPO_4$, 2.68 mM KCl, and 1.47 mM $KH_2PO_4$). Two microliters of this diluted serum was added to 200 µL of a diluent, so that the serum was finally diluted 30000 times. One hundred microliters of the finally diluted serum was added to each well, followed by incubation at room temperature for 2 hours. Then, aspiration and washing were repeated 5 times using a washing solution (300 µL of wash buffer/well). The wash buffer composition was 100 mL of wash buffer/1900 mL of ultrapure water, 20 times dilution. Each well was filled with 100 µL of Working Detector previously prepared by mixing 12 mL of biotinylated anti-human C4a polyclonal antibody and 48 µL of 250× concentrated Streptavidin-horseradish peroxidase conjugate, followed by incubation at room temperature for 1 hour. Aspiration and washing were repeated seven times as in above. Subsequently, 100 µL of a TMB substrate was added to each well, followed by shaking for 5 seconds and then incubation (dark room) at room temperature for 30 minutes. While luminescence is observed, 50 µL of Stop Solution were added. After the color reaction, absorbance at a wavelength of 450 nm was measured. The C4a level in the serum was calculated from a calibration curve prepared using standard materials. The statistic analysis was performed by a Mann-Whitney U test, and $P<0.05$ was determined to be statistically significant.

(2) Results

Figure 15:
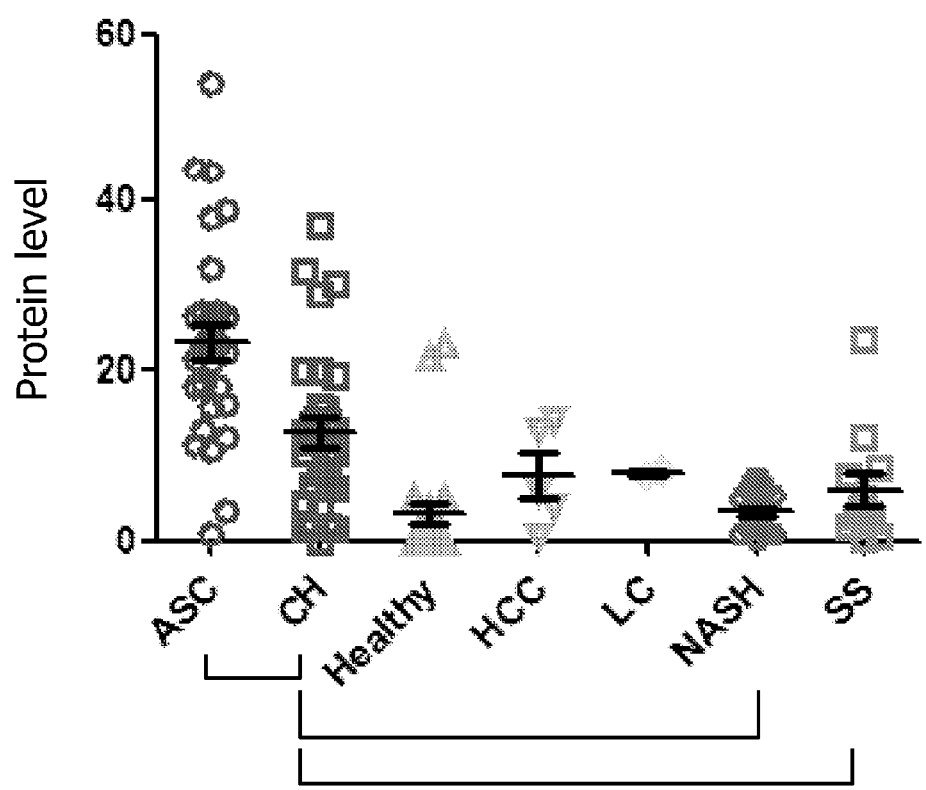
FIG. 15 is a graph showing the results of detection of the C4a protein level in sera by ELISA (BD OptEIA ELISA Kit).

FIG. 15 shows C4a protein levels in the sera. The levels are high ($P<0.05$) in ASCs compared to those in the healthy individuals. Therefore, the measurement of blood C4a level made it possible to discriminate ASCs from other diseases as a diagnostic marker of an ASC. These results suggest that the C4a level may be a high value marker of an ASC.

Next, the serum C4a levels were calculated, and the results thereof showed that C4a protein level decreased with aggravation of symptoms: ASCs, patients with hepatitis, patients with liver cirrhosis, and patients with hepatocellular carcinoma, in the order toward the clinical deterioration. In particular, a significant difference was also observed between two groups of ASC and hepatitis ($P<0.05$). Evidently, peak intensities plotted for each sample are notably high in ASC (FIG. 15). In addition, as shown in FIG. 15, a significant difference is found between NASH and chronic hepatitis (CH) at $P<0.05$, while a significant difference was found between SS and chronic hepatitis (CH) at $P<0.05$.

[4] Detection of Partial Peptide Derived from C4 Using Protein Chip System

A protein chip system (Bio-Rad) consists of a protein chip and SELDI and is useful for screening serum diagnostic markers, like ClinProt. The chip surface is labeled with various functional groups and captures proteins and peptides in a serum applied thereto. Peaks are detected by measurement with the SELDI. Consequently, detection of partial peptide peaks (1738 m/z and 1896 m/z) derived from C4 were investigated by the protein chip system.

(1) Material and Method

Specimens used were sera of ASCs and healthy individuals. The serum was applied to the protein chip as follows. Five microliters of the serum was added to 45 µL of a urea buffer (7 M urea, 2 M thiourea, 4% CHAPS, 1% DTT, and 2% Ampholyte). The mixture was left to stand on an ice bath for 10 minutes to denature the serum proteins and then was diluted with 450 µL of 50 mM sodium acetate at a pH of 4.5. One hundred microliters of the diluted solution was added to a cation exchange chip CM10 (Bio-Rad) equilibrated in advance. After osmotic treatment at room temperature for 30 minutes, the CM10 was washed with 50 mM sodium acetate at a pH of 4.5 three times and further with ultrapure water twice. After air drying, 0.5 µL of 50% saturated CCA were added to the spots twice to prepare a crystal mixture of the peptides and CCA. The peaks were detected with SELDI.

The peak intensities of the ASC and the healthy individual groups were investigated with biomarker Wizard software (Bio-Rad). In comparison of a plurality of mass spectra, peaks having m/z values that were in agreement with each other within an error of 0.3% were recognized as being derived from the same molecule. The significant difference between the groups was investigated by a Mann-Whitney U test, and peaks were determined to be significant at $P<0.05$.

(2) Results

Peaks ($P<0.05$) that significantly increase, in particular, in the ASC group were selected from the spectra of the ASC group and the healthy individual group, and peaks having a peak intensity of 5 or more were selected. Table 6 shows the results of identification of the peaks, and FIG. 16 shows typical spectral patterns of ASC and a healthy individual. FIG. 16(A) demonstrates that the peaks at 1738 m/z and 1896 m/z derived from C4 significantly increase in the ASC compared to the healthy individuals (Table 6). FIG. 16(C) evidently demonstrates that the peak intensities plotted for each sample are also remarkably high in the ASC.

TABLE 6

Peaks with increasing expression in ASC (Protein chip)

| Molecular weight m/z | ASC (n = 20) Peak intensity | Healthy individual (n = 10) Peak intensity | P value |
|---|---|---|---|
| 1738 | 25.57 ± 9.13 | 6.74 ± 5.40 | $5.5 \times 10^{-3}$ |
| 1863 | 10.57 ± 3.79 | 4.98 ± 2.28 | $1.8 \times 10^{-4}$ |
| 1896 | 10.70 ± 10.23 | 2.34 ± 2.38 | $3.7 \times 10^{-5}$ |
| 1817 | 19.75 ± 10.34 | 3.42 ± 7.48 | $1.1 \times 10^{-5}$ |
| 1942 | 14.63 ± 9.02 | 4.65 ± 9.81 | $1.3 \times 10^{-5}$ |
| 2079 | 8.49 ± 4.04 | 5.72 ± 6.89 | $1.9 \times 10^{-5}$ |
| 2207 | 7.04 ± 4.35 | 2.27 ± 2.99 | $1.5 \times 10^{-4}$ |
| 2858 | 24.58 ± 9.80 | 13.78 ± 8.02 | $2.4 \times 10^{-3}$ |

Example 3

Diagnosis by ELISA Using Anti-Kininogen Antibody

An example for discriminating between a healthy individual and a patient with NAFLD using an antibody against the kininogen as a kininogen-based marker will be described.

(1) Material and Method

Sera of 11 healthy individuals, 5 NASH subjects, and 5 simple steatosis subjects were used as specimens.

Figure 18:
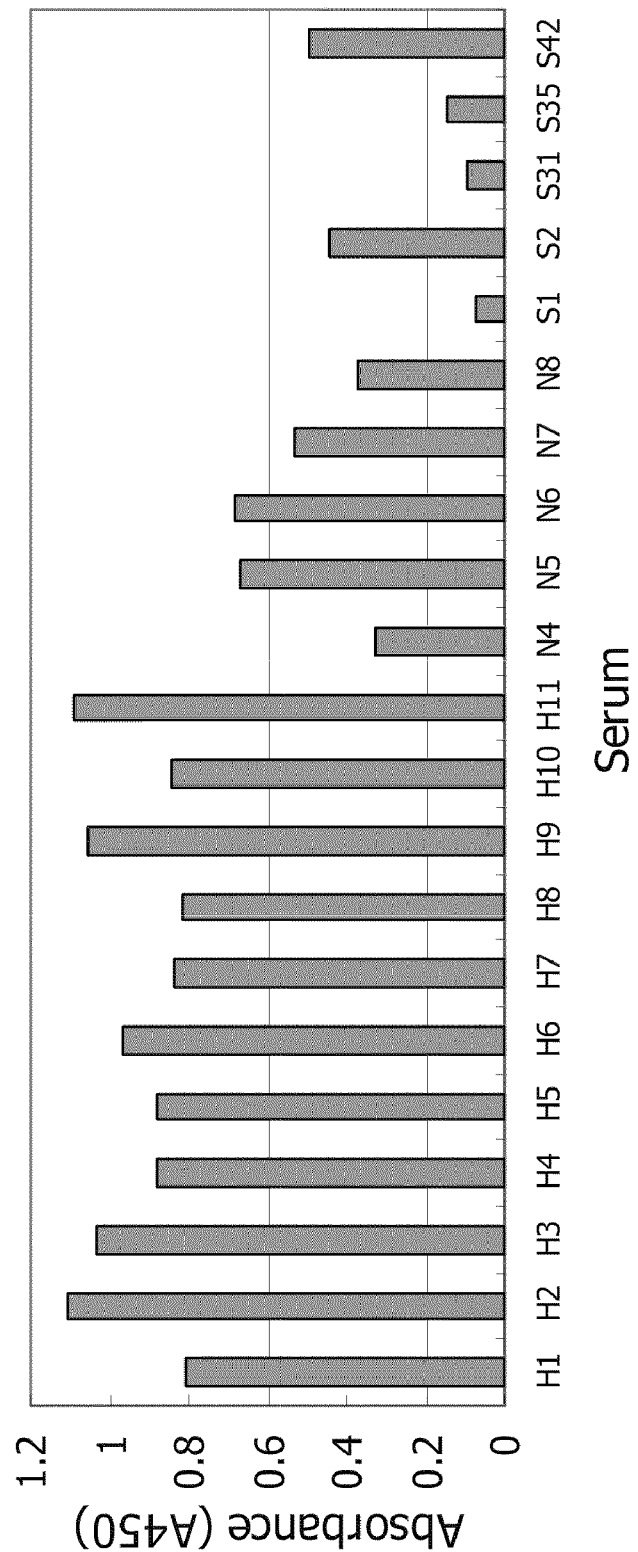
FIG. 18 is a graph showing discrimination between patients with NAFLD and healthy individuals by kininogen-based ELISA.

An anti-human kininogen monoclonal antibody (manufactured by R&D, Catalog Number: MAB1569) was diluted with an immobilization buffer (Sumitomo Bakelite) into 1 µg/mL, and the diluted antibody solution was applied to a plate of New ELISA Plate B (Sumitomo Bakelite) in an amount of 100 µL/well, followed by leaving to stand at room temperature for 1 to 2 hours. The plate was washed with 300 µL of PBSx (PBS (phosphate buffered saline) containing 0.05% Triton-X100) three times. Then, the serum specimen was diluted 200 times with PBS and was added to each well in an amount of 100 µL/well, followed by leaving to stand at room temperature for 1 hour. The plate was washed with 300 µL of PBSx three times. An anti-KIG1 antibody (manufactured by Sigma, Catalog Number: HAP001616) diluted 1000 times with PBS was added to each well in an amount of 100 µL/well, followed by leaving to stand at room temperature for 1 hour. Then, the plate was washed with 300 µL of PBSx three times. Subsequently, a goat-anti-rabbit IgG HRP conjugate antibody (manufactured by Santa Cruz Biotechnology, Catalog Number: sc-2004) diluted 1000 times with PBS was added to each well in an amount of 100 µL/well, followed by leaving to stand at room temperature for 1 hour. Then, the plate was treated with 300 µL of PBSx (PBS containing 0.05% Triton-X100) three times for washing. Finally, Ultra-TMB-ELISA (manufactured by PIERCE, Catalog Number: 34028) was added to each well in an amount of 100 µL/well. After leaving to stand for 15 to 50 minutes, the reaction was terminated by adding 50 µL of 2 M sulfuric acid, followed by colorimetry at 450 nm (2) Results From the results described above, H1 to H11, which were sera of healthy individuals, yielded an average±standard deviation of 0.937±0.117. In addition, N4 to S42, in which N means NASH and S means simple steatosis, yielded an average±standard deviation of 0.383±0.224. From FIG. 18, the kininogen of the healthy individuals is determined to be approximately 1, and that of patients with NAFLD is determined to be approximately 0.5 or less.

INDUSTRIAL APPLICABILITY

Figure 17:
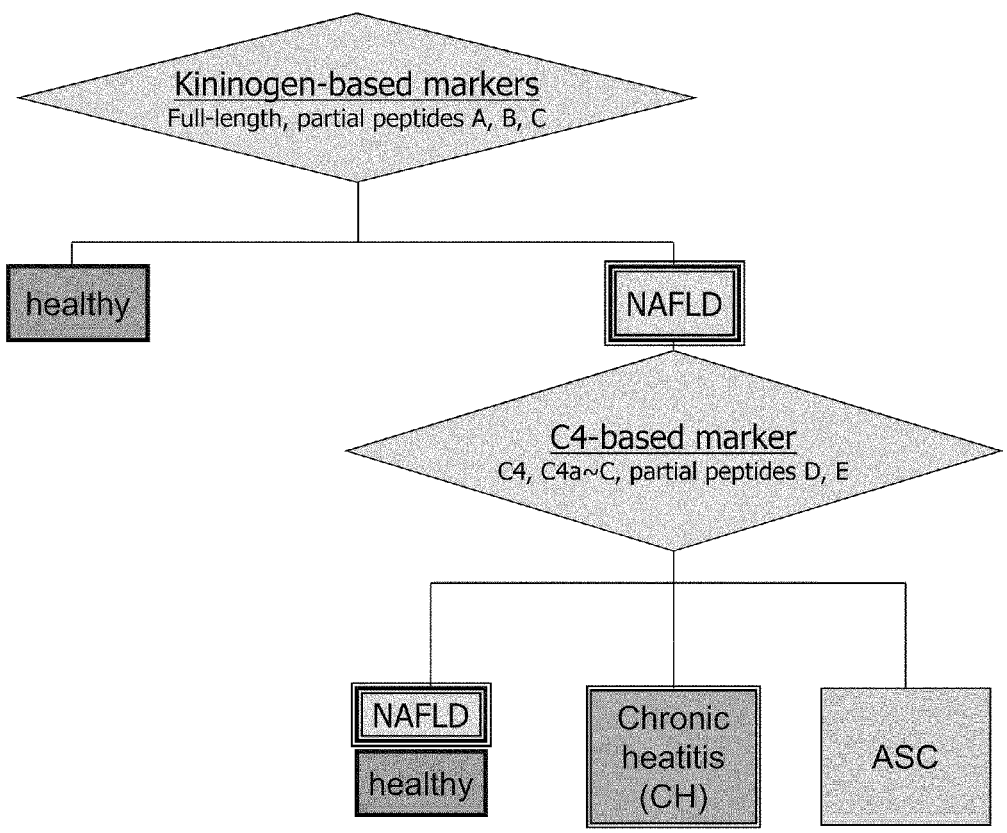
FIG. 17 is a schematic diagram (multimarker system) of a flow for identification of liver diseases using kininogen-based and C4-based markers of the present invention.

All the kininogen-based full length and the partial peptides A, B, and C of the present invention show significant differences in serum levels thereof between healthy individuals and patients with NAFLD and thus may be served as useful markers for NAFLD diagnosis. These may be used not only for diagnosis by physicians but also measurement or assay of blood or serum. Furthermore, as shown in FIG. 17, combination of the kininogen-based marker and the C4-based marker may conveniently discriminate between an ASC, a patient with hepatitis, a patient with liver cirrhosis, a patient with hepatocellular carcinoma, a patient with NAFLD, and a healthy individual. The convenient detecting method provided by the marker of the present invention enables medical examination of many subjects in pre-disease conditions and may be preferably applied to early diagnosis for discriminating between healthy individuals and patients with NAFLD, patients with CH, or ASCs and may be used for early detection of these lifestyle-related diseases or liver diseases caused therefrom.

---

The invention claimed is:

1. A detecting method for identification of a non-alcoholic fatty liver disease (NAFLD) in a subject, the method comprising detecting an increase in the serum level of at least one partial peptide selected from the group consisting of partial peptide A (SEQ ID NO:2), B (SEQ ID NO:3) and C (SEQ ID NO:4) in said subject relative to the serum level of such partial peptide in a healthy individual, said increase being indicative of NAFLD.

2. The detecting method according to claim 1, wherein the detection is performed by ELISA.

3. The detecting method of claim 1 wherein the partial peptide is sequence A (SEQ ID NO:2).

4. The method of claim 1, wherein said detecting is achieved by MS/MS analysis.

5. The method of claim 4 in which the ionization principle is matrix-associated laser desorption/ionization (MALDI) and the mass-separation principle is time of flight (TOF).

6. The method of claim 1, wherein said detecting is an immunochemical detection process.

7. The method of claim 6, wherein at least one of said partial peptides is used as a diagnostic agent in said immunochemical detection process.

8. The method of claim 6 wherein an antibody recognizing at least one of said partial peptides as an antigen is used as a diagnostic agent in said immunochemical detection process.

9. The method according to claim 8, wherein the antibody is a polyclonal antibody that is obtained by immunizing a rabbit with at least one partial peptide selected from the group consisting of the partial peptide A (SEQ ID NO:2), the partial peptide B (SEQ ID NO:3), and the partial peptide C (SEQ ID NO:4).

10. The method according to claim 8, wherein the antibody is a monoclonal antibody that is obtained by immunizing a mouse with at least one partial peptide selected from the group consisting of the partial peptide A (SEQ ID NO:2), the partial peptide B (SEQ ID NO:3), and the partial peptide C (SEQ ID NO:4).

11. The method of claim 8 wherein the antibody is immobilized on the surface of a solid phase.

12. The method of claim 1 wherein the diagnosis of NAFLD is based on an increase which is more than a standard deviation above the average level for healthy individuals.

13. A detecting method for identification of a non-alcoholic fatty liver disease (NAFLD) in a subject which comprises (a) detecting a decrease in the serum level in said subject of full length high molecular weight kininogen, relative to the level in a healthy individual, or
(b) detecting an increase in the serum level in said subject of at least one partial peptide selected from the group consisting of partial peptide A (SEQ ID NO:2), B (SEQ ID NO:3) and C (SEQ ID NO:4), relative to the level in a healthy individual, said decrease of (a) or increase of (b) being indicative of NAFLD.

14. The detecting method of claim 13, step (a) using a high molecular weight kininogen diagnostic agent selected from the group consisting of high molecular weight kininogen and an antibody recognizing said high molecular weight kininogen.

15. The detecting method according to claim 14, the method further using as the second diagnostic agent an antibody that recognizes the high-molecular-weight kininogen in a sample but does not recognize any of the partial peptide A, the partial peptide B, and the partial peptide C.

16. The method of claim 13, comprising both (a) and (b).

* * * * *

SEQUENCE LISTING

```
<160> NUMBER OF SEQ ID NOS: 8

<210> SEQ ID NO 1
<211> LENGTH: 644
<212> TYPE: PRT
<213> ORGANISM: Homo sapiens

<400> SEQUENCE: 1

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Cys Asn Asp Lys Asp
            20                  25                  30

Leu Phe Lys Ala Val Asp Ala Ala Leu Lys Lys Tyr Asn Ser Gln Asn
        35                  40                  45

Gln Ser Asn Asn Gln Phe Val Leu Tyr Arg Ile Thr Glu Ala Thr Lys
    50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
                85                  90                  95

Lys Asp Ala Ala Lys Ala Ala Thr Gly Glu Cys Thr Ala Thr Val Gly
            100                 105                 110

Lys Arg Ser Ser Thr Lys Phe Ser Val Ala Thr Gln Thr Cys Gln Ile
            115                 120                 125
```

```
Thr Pro Ala Glu Gly Pro Val Val Thr Ala Gln Tyr Asp Cys Leu Gly
    130                 135                 140

Cys Val His Pro Ile Ser Thr Gln Ser Pro Asp Leu Glu Pro Ile Leu
145                 150                 155                 160

Arg His Gly Ile Gln Tyr Phe Asn Asn Thr Gln His Ser Ser Leu
            165                 170                 175

Phe Met Leu Asn Glu Val Lys Arg Ala Gln Arg Gln Val Val Ala Gly
            180                 185                 190

Leu Asn Phe Arg Ile Thr Tyr Ser Ile Val Gln Thr Asn Cys Ser Lys
            195                 200                 205

Glu Asn Phe Leu Phe Leu Thr Pro Asp Cys Lys Ser Leu Trp Asn Gly
            210                 215                 220

Asp Thr Gly Glu Cys Thr Asp Asn Ala Tyr Ile Asp Ile Gln Leu Arg
225                 230                 235                 240

Ile Ala Ser Phe Ser Gln Asn Cys Asp Ile Tyr Pro Gly Lys Asp Phe
                245                 250                 255

Val Gln Pro Pro Thr Lys Ile Cys Val Gly Cys Pro Arg Asp Ile Pro
            260                 265                 270

Thr Asn Ser Pro Glu Leu Glu Thr Leu Thr His Thr Ile Thr Lys
            275                 280                 285

Leu Asn Ala Glu Asn Asn Ala Thr Phe Tyr Phe Lys Ile Asp Asn Val
    290                 295                 300

Lys Lys Ala Arg Val Gln Val Ala Gly Lys Lys Tyr Phe Ile Asp
305                 310                 315                 320

Phe Val Ala Arg Glu Thr Thr Cys Ser Lys Glu Ser Asn Glu Glu Leu
                325                 330                 335

Thr Glu Ser Cys Glu Thr Lys Lys Leu Gly Gln Ser Leu Asp Cys Asn
            340                 345                 350

Ala Glu Val Tyr Val Val Pro Trp Glu Lys Lys Ile Tyr Pro Thr Val
            355                 360                 365

Asn Cys Gln Pro Leu Gly Met Ile Ser Leu Met Lys Arg Pro Pro Gly
    370                 375                 380

Phe Ser Pro Phe Arg Ser Arg Ile Gly Glu Ile Lys Glu Glu Thr
385                 390                 395                 400

Thr Val Ser Pro Pro His Thr Ser Met Ala Pro Ala Gln Asp Glu Glu
                405                 410                 415

Arg Asp Ser Gly Lys Glu Gln Gly His Thr Arg Arg His Asp Trp Gly
            420                 425                 430

His Glu Lys Gln Arg Lys His Asn Leu Gly His Gly His Lys His Glu
    435                 440                 445

Arg Asp Gln Gly His Gly His Gln Arg Gly His Gly Leu Gly His Gly
    450                 455                 460

His Glu Gln Gln His Gly Leu Gly His Gly His Lys Phe Lys Leu Asp
465                 470                 475                 480

Asp Asp Leu Glu His Gln Gly Gly His Val Leu Asp His Gly His Lys
                485                 490                 495

His Lys His Gly His Gly His Gly Lys His Lys Asn Lys Gly Lys Lys
            500                 505                 510

Asn Gly Lys His Asn Gly Trp Lys Thr Glu His Leu Ala Ser Ser Ser
            515                 520                 525

Glu Asp Ser Thr Thr Pro Ser Ala Gln Thr Gln Glu Lys Thr Glu Gly
    530                 535                 540

Pro Thr Pro Ile Pro Ser Leu Ala Lys Pro Gly Val Thr Val Thr Phe
```

```
            545                 550                 555                 560
Ser Asp Phe Gln Asp Ser Asp Leu Ile Ala Thr Met Met Pro Pro Ile
                565                 570                 575

Ser Pro Ala Pro Ile Gln Ser Asp Asp Trp Ile Pro Asp Ile Gln
            580                 585                 590

Ile Asp Pro Asn Gly Leu Ser Phe Asn Pro Ile Ser Asp Phe Pro Asp
            595                 600                 605

Thr Thr Ser Pro Lys Cys Pro Gly Arg Pro Trp Lys Ser Val Ser Glu
            610                 615                 620

Ile Asn Pro Thr Thr Gln Met Lys Glu Ser Tyr Tyr Phe Asp Leu Thr
625                 630                 635                 640

Asp Gly Leu Ser

<210> SEQ ID NO 2
<211> LENGTH: 17
<212> TYPE: PRT
<213> ORGANISM: Homo sapiens

<400> SEQUENCE: 2

Asn Leu Gly His Gly His Lys His Glu Arg Asp Gln Gly His Gly His
1               5                   10                  15

Gln

<210> SEQ ID NO 3
<211> LENGTH: 18
<212> TYPE: PRT
<213> ORGANISM: Homo sapiens

<400> SEQUENCE: 3

His Asn Leu Gly His Gly His Lys His Glu Arg Asp Gln Gly His Gly
1               5                   10                  15

His Gln

<210> SEQ ID NO 4
<211> LENGTH: 19
<212> TYPE: PRT
<213> ORGANISM: Homo sapiens

<400> SEQUENCE: 4

Lys His Asn Leu Gly His Gly His Lys His Glu Arg Asp Gln Gly His
1               5                   10                  15

Gly His Gln

<210> SEQ ID NO 5
<211> LENGTH: 1744
<212> TYPE: PRT
<213> ORGANISM: Homo sapiens

<400> SEQUENCE: 5

Met Arg Leu Leu Trp Gly Leu Ile Trp Ala Ser Ser Phe Phe Thr Leu
1               5                   10                  15

Ser Leu Gln Lys Pro Arg Leu Leu Leu Phe Ser Pro Ser Val Val His
                20                  25                  30

Leu Gly Val Pro Leu Ser Val Gly Val Gln Leu Gln Asp Val Pro Arg
            35                  40                  45

Gly Gln Val Val Lys Gly Ser Val Phe Leu Arg Asn Pro Ser Arg Asn
        50                  55                  60

Asn Val Pro Cys Ser Pro Lys Val Asp Phe Thr Leu Ser Ser Glu Arg
65                  70                  75                  80
```

```
Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
    130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
    210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
        275                 280                 285

Glu Asp Gly Lys Lys Thr Phe Phe Arg Gly Leu Glu Ser Gln Thr Lys
    290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ala Ile Ile Glu Ser Pro Gly Gly Glu Met
            340                 345                 350

Glu Glu Ala Glu Leu Thr Ser Trp Tyr Phe Val Ser Ser Pro Phe Ser
        355                 360                 365

Leu Asp Leu Ser Lys Thr Lys Arg His Leu Val Pro Gly Ala Pro Phe
    370                 375                 380

Leu Leu Gln Ala Leu Val Arg Glu Met Ser Gly Ser Pro Ala Ser Gly
385                 390                 395                 400

Ile Pro Val Lys Val Ser Ala Thr Val Ser Ser Pro Gly Ser Val Pro
                405                 410                 415

Glu Val Gln Asp Ile Gln Gln Asn Thr Asp Gly Ser Gly Gln Val Ser
            420                 425                 430

Ile Pro Ile Ile Ile Pro Gln Thr Ile Ser Glu Leu Gln Leu Ser Val
        435                 440                 445

Ser Ala Gly Ser Pro His Pro Ala Ile Ala Arg Leu Thr Val Ala Ala
    450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
                485                 490                 495

Gly Ser Gly Ala Thr Phe Ser His Tyr Tyr Tyr Met Ile Leu Ser Arg
```

```
                500                 505                 510
Gly Gln Ile Val Phe Met Asn Arg Glu Pro Lys Arg Thr Leu Thr Ser
            515                 520                 525

Val Ser Val Phe Val Asp His His Leu Ala Pro Ser Phe Tyr Phe Val
            530                 535                 540

Ala Phe Tyr Tyr His Gly Asp His Pro Val Ala Asn Ser Leu Arg Val
545                 550                 555                 560

Asp Val Gln Ala Gly Ala Cys Glu Gly Lys Leu Glu Leu Ser Val Asp
            565                 570                 575

Gly Ala Lys Gln Tyr Arg Asn Gly Glu Ser Val Lys Leu His Leu Glu
            580                 585                 590

Thr Asp Ser Leu Ala Leu Val Ala Leu Gly Ala Leu Asp Thr Ala Leu
            595                 600                 605

Tyr Ala Ala Gly Ser Lys Ser His Lys Pro Leu Asn Met Gly Lys Val
610                 615                 620

Phe Glu Ala Met Asn Ser Tyr Asp Leu Gly Cys Gly Pro Gly Gly Gly
625                 630                 635                 640

Asp Ser Ala Leu Gln Val Phe Gln Ala Ala Gly Leu Ala Phe Ser Asp
            645                 650                 655

Gly Asp Gln Trp Thr Leu Ser Arg Lys Arg Leu Ser Cys Pro Lys Glu
            660                 665                 670

Lys Thr Thr Arg Lys Lys Arg Asn Val Asn Phe Gln Lys Ala Ile Asn
            675                 680                 685

Glu Lys Leu Gly Gln Tyr Ala Ser Pro Thr Ala Lys Arg Cys Cys Gln
            690                 695                 700

Asp Gly Val Thr Arg Leu Pro Met Met Arg Ser Cys Glu Gln Arg Ala
705                 710                 715                 720

Ala Arg Val Gln Gln Pro Asp Cys Arg Glu Pro Phe Leu Ser Cys Cys
            725                 730                 735

Gln Phe Ala Glu Ser Leu Arg Lys Lys Ser Arg Asp Lys Gly Gln Ala
            740                 745                 750

Gly Leu Gln Arg Ala Leu Glu Ile Leu Gln Glu Asp Leu Ile Asp
            755                 760                 765

Glu Asp Asp Ile Pro Val Arg Ser Phe Phe Pro Glu Asn Trp Leu Trp
770                 775                 780

Arg Val Glu Thr Val Asp Arg Phe Gln Ile Leu Thr Leu Trp Leu Pro
785                 790                 795                 800

Asp Ser Leu Thr Thr Trp Glu Ile His Gly Leu Ser Leu Ser Lys Thr
            805                 810                 815

Lys Gly Leu Cys Val Ala Thr Pro Val Gln Leu Arg Val Phe Arg Glu
            820                 825                 830

Phe His Leu His Leu Arg Leu Pro Met Ser Val Arg Arg Phe Glu Gln
            835                 840                 845

Leu Glu Leu Arg Pro Val Leu Tyr Asn Tyr Leu Asp Lys Asn Leu Thr
            850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
            885                 890                 895

Val Ala Phe Ser Val Val Pro Thr Ala Ala Ala Val Ser Leu Lys
            900                 905                 910

Val Val Ala Arg Gly Ser Phe Glu Phe Pro Val Gly Asp Ala Val Ser
            915                 920                 925
```

```
Lys Val Leu Gln Ile Glu Lys Glu Gly Ala Ile His Arg Glu Glu Leu
        930                 935                 940
Val Tyr Glu Leu Asn Pro Leu Asp His Arg Gly Arg Thr Leu Glu Ile
945                 950                 955                 960
Pro Gly Asn Ser Asp Pro Asn Met Ile Pro Asp Gly Asp Phe Asn Ser
                965                 970                 975
Tyr Val Arg Val Thr Ala Ser Asp Pro Leu Asp Thr Leu Gly Ser Glu
            980                 985                 990
Gly Ala Leu Ser Pro Gly Gly Val Ala Ser Leu Leu Arg Leu Pro Arg
        995                 1000                1005
Gly Cys Gly Glu Gln Thr Met Ile Tyr Leu Ala Pro Thr Leu Ala
        1010                1015                1020
Ala Ser Arg Tyr Leu Asp Lys Thr Glu Gln Trp Ser Thr Leu Pro
        1025                1030                1035
Pro Glu Thr Lys Asp His Ala Val Asp Leu Ile Gln Lys Gly Tyr
        1040                1045                1050
Met Arg Ile Gln Gln Phe Arg Lys Ala Asp Gly Ser Tyr Ala Ala
        1055                1060                1065
Trp Leu Ser Arg Asp Ser Ser Thr Trp Leu Thr Ala Phe Val Leu
        1070                1075                1080
Lys Val Leu Ser Leu Ala Gln Glu Gln Val Gly Gly Ser Pro Glu
        1085                1090                1095
Lys Leu Gln Glu Thr Ser Asn Trp Leu Leu Ser Gln Gln Gln Ala
        1100                1105                1110
Asp Gly Ser Phe Gln Asp Pro Cys Pro Val Leu Asp Arg Ser Met
        1115                1120                1125
Gln Gly Gly Leu Val Gly Asn Asp Glu Thr Val Ala Leu Thr Ala
        1130                1135                1140
Phe Val Thr Ile Ala Leu His His Gly Leu Ala Val Phe Gln Asp
        1145                1150                1155
Glu Gly Ala Glu Pro Leu Lys Gln Arg Val Glu Ala Ser Ile Ser
        1160                1165                1170
Lys Ala Asn Ser Phe Leu Gly Glu Lys Ala Ser Ala Gly Leu Leu
        1175                1180                1185
Gly Ala His Ala Ala Ala Ile Thr Ala Tyr Ala Leu Ser Leu Thr
        1190                1195                1200
Lys Ala Pro Val Asp Leu Leu Gly Val Ala His Asn Asn Leu Met
        1205                1210                1215
Ala Met Ala Gln Glu Thr Gly Asp Asn Leu Tyr Trp Gly Ser Val
        1220                1225                1230
Thr Gly Ser Gln Ser Asn Ala Val Ser Pro Thr Pro Ala Pro Arg
        1235                1240                1245
Asn Pro Ser Asp Pro Met Pro Gln Ala Pro Ala Leu Trp Ile Glu
        1250                1255                1260
Thr Thr Ala Tyr Ala Leu Leu His Leu Leu Leu His Glu Gly Lys
        1265                1270                1275
Ala Glu Met Ala Asp Gln Ala Ser Ala Trp Leu Thr Arg Gln Gly
        1280                1285                1290
Ser Phe Gln Gly Gly Phe Arg Ser Thr Gln Asp Thr Val Ile Ala
        1295                1300                1305
Leu Asp Ala Leu Ser Ala Tyr Trp Ile Ala Ser His Thr Thr Glu
        1310                1315                1320
Glu Arg Gly Leu Asn Val Thr Leu Ser Ser Thr Gly Arg Asn Gly
        1325                1330                1335
```

-continued

Phe Lys Ser His Ala Leu Gln Leu Asn Asn Arg Gln Ile Arg Gly
    1340            1345                1350

Leu Glu Glu Glu Leu Gln Phe Ser Leu Gly Ser Lys Ile Asn Val
    1355            1360                1365

Lys Val Gly Gly Asn Ser Lys Gly Thr Leu Lys Val Leu Arg Thr
    1370            1375                1380

Tyr Asn Val Leu Asp Met Lys Asn Thr Thr Cys Gln Asp Leu Gln
    1385            1390                1395

Ile Glu Val Thr Val Lys Gly His Val Glu Tyr Thr Met Glu Ala
    1400            1405                1410

Asn Glu Asp Tyr Glu Asp Glu Tyr Asp Glu Leu Pro Ala Lys
    1415            1420                1425

Asp Asp Pro Asp Ala Pro Leu Gln Pro Val Thr Pro Leu Gln Leu
    1430            1435                1440

Phe Glu Gly Arg Arg Asn Arg Arg Arg Glu Ala Pro Lys Val
    1445            1450                1455

Val Glu Glu Gln Glu Ser Arg Val His Tyr Thr Val Cys Ile Trp
    1460            1465                1470

Arg Asn Gly Lys Val Gly Leu Ser Gly Met Ala Ile Ala Asp Val
    1475            1480                1485

Thr Leu Leu Ser Gly Phe His Ala Leu Arg Ala Asp Leu Glu Lys
    1490            1495                1500

Leu Thr Ser Leu Ser Asp Arg Tyr Val Ser His Phe Glu Thr Glu
    1505            1510                1515

Gly Pro His Val Leu Leu Tyr Phe Asp Ser Val Pro Thr Ser Arg
    1520            1525                1530

Glu Cys Val Gly Phe Glu Ala Val Gln Glu Val Pro Val Gly Leu
    1535            1540                1545

Val Gln Pro Ala Ser Ala Thr Leu Tyr Asp Tyr Tyr Asn Pro Glu
    1550            1555                1560

Arg Arg Cys Ser Val Phe Tyr Gly Ala Pro Ser Lys Ser Arg Leu
    1565            1570                1575

Leu Ala Thr Leu Cys Ser Ala Glu Val Cys Gln Cys Ala Glu Gly
    1580            1585                1590

Lys Cys Pro Arg Gln Arg Arg Ala Leu Glu Arg Gly Leu Gln Asp
    1595            1600                1605

Glu Asp Gly Tyr Arg Met Lys Phe Ala Cys Tyr Tyr Pro Arg Val
    1610            1615                1620

Glu Tyr Gly Phe Gln Val Lys Val Leu Arg Glu Asp Ser Arg Ala
    1625            1630                1635

Ala Phe Arg Leu Phe Glu Thr Lys Ile Thr Gln Val Leu His Phe
    1640            1645                1650

Thr Lys Asp Val Lys Ala Ala Ala Asn Gln Met Arg Asn Phe Leu
    1655            1660                1665

Val Arg Ala Ser Cys Arg Leu Arg Leu Glu Pro Gly Lys Glu Tyr
    1670            1675                1680

Leu Ile Met Gly Leu Asp Gly Ala Thr Tyr Asp Leu Glu Gly His
    1685            1690                1695

Pro Gln Tyr Leu Leu Asp Ser Asn Ser Trp Ile Glu Glu Met Pro
    1700            1705                1710

Ser Glu Arg Leu Cys Arg Ser Thr Arg Gln Arg Ala Ala Cys Ala
    1715            1720                1725

Gln Leu Asn Asp Phe Leu Gln Glu Tyr Gly Thr Gln Gly Cys Gln

```
            1730            1735            1740
Val

<210> SEQ ID NO 6
<211> LENGTH: 1744
<212> TYPE: PRT
<213> ORGANISM: Homo sapiens

<400> SEQUENCE: 6

Met Arg Leu Leu Trp Gly Leu Ile Trp Ala Ser Ser Phe Phe Thr Leu
1               5                   10                  15

Ser Leu Gln Lys Pro Arg Leu Leu Phe Ser Pro Ser Val Val His
            20                  25                  30

Leu Gly Val Pro Leu Ser Val Gly Val Gln Leu Gln Asp Val Pro Arg
            35                  40                  45

Gly Gln Val Val Lys Gly Ser Val Phe Leu Arg Asn Pro Ser Arg Asn
        50                  55                  60

Asn Val Pro Cys Ser Pro Lys Val Asp Phe Thr Leu Ser Ser Glu Arg
65                  70                  75                  80

Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
        275                 280                 285

Glu Asp Gly Lys Lys Thr Phe Phe Arg Gly Leu Glu Ser Gln Thr Lys
290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ala Ile Ile Glu Ser Pro Gly Gly Glu Met
            340                 345                 350

Glu Glu Ala Glu Leu Thr Ser Trp Tyr Phe Val Ser Ser Pro Phe Ser
        355                 360                 365
```

-continued

```
Leu Asp Leu Ser Lys Thr Lys Arg His Leu Val Pro Gly Ala Pro Phe
    370                 375                 380
Leu Leu Gln Ala Leu Val Arg Glu Met Ser Gly Ser Pro Ala Ser Gly
385                 390                 395                 400
Ile Pro Val Lys Val Ser Ala Thr Val Ser Ser Pro Gly Ser Val Pro
                405                 410                 415
Glu Val Gln Asp Ile Gln Gln Asn Thr Asp Gly Ser Gly Gln Val Ser
            420                 425                 430
Ile Pro Ile Ile Ile Pro Gln Thr Ile Ser Glu Leu Gln Leu Ser Val
        435                 440                 445
Ser Ala Gly Ser Pro His Pro Ala Ile Ala Arg Leu Thr Val Ala Ala
450                 455                 460
Pro Pro Ser Gly Gly Pro Gly Phe Leu Ser Ile Glu Arg Pro Asp Ser
465                 470                 475                 480
Arg Pro Pro Arg Val Gly Asp Thr Leu Asn Leu Asn Leu Arg Ala Val
                485                 490                 495
Gly Ser Gly Ala Thr Phe Ser His Tyr Tyr Tyr Met Ile Leu Ser Arg
            500                 505                 510
Gly Gln Ile Val Phe Met Asn Arg Glu Pro Lys Arg Thr Leu Thr Ser
        515                 520                 525
Val Ser Val Phe Val Asp His His Leu Ala Pro Ser Phe Tyr Phe Val
530                 535                 540
Ala Phe Tyr Tyr His Gly Asp His Pro Val Ala Asn Ser Leu Arg Val
545                 550                 555                 560
Asp Val Gln Ala Gly Ala Cys Glu Gly Lys Leu Glu Leu Ser Val Asp
                565                 570                 575
Gly Ala Lys Gln Tyr Arg Asn Gly Glu Ser Val Lys Leu His Leu Glu
            580                 585                 590
Thr Asp Ser Leu Ala Leu Val Ala Leu Gly Ala Leu Asp Thr Ala Leu
        595                 600                 605
Tyr Ala Ala Gly Ser Lys Ser His Lys Pro Leu Asn Met Gly Lys Val
610                 615                 620
Phe Glu Ala Met Asn Ser Tyr Asp Leu Gly Cys Gly Pro Gly Gly Gly
625                 630                 635                 640
Asp Ser Ala Leu Gln Val Phe Gln Ala Ala Gly Leu Ala Phe Ser Asp
                645                 650                 655
Gly Asp Gln Trp Thr Leu Ser Arg Lys Arg Leu Ser Cys Pro Lys Glu
            660                 665                 670
Lys Thr Thr Arg Lys Lys Arg Asn Val Asn Phe Gln Lys Ala Ile Asn
        675                 680                 685
Glu Lys Leu Gly Gln Tyr Ala Ser Pro Thr Ala Lys Arg Cys Cys Gln
690                 695                 700
Asp Gly Val Thr Arg Leu Pro Met Met Arg Ser Cys Glu Gln Arg Ala
705                 710                 715                 720
Ala Arg Val Gln Gln Pro Asp Cys Arg Glu Pro Phe Leu Ser Cys Cys
                725                 730                 735
Gln Phe Ala Glu Ser Leu Arg Lys Lys Ser Arg Asp Lys Gly Gln Ala
            740                 745                 750
Gly Leu Gln Arg Ala Leu Glu Ile Leu Gln Glu Asp Leu Ile Asp
        755                 760                 765
Glu Asp Asp Ile Pro Val Arg Ser Phe Phe Pro Glu Asn Trp Leu Trp
770                 775                 780
Arg Val Glu Thr Val Asp Arg Phe Gln Ile Leu Thr Leu Trp Leu Pro
```

-continued

```
            785                 790                 795                 800
Asp Ser Leu Thr Thr Trp Glu Ile His Gly Leu Ser Leu Ser Lys Thr
                    805                 810                 815
Lys Gly Leu Cys Val Ala Thr Pro Val Gln Leu Arg Val Phe Arg Glu
                820                 825                 830
Phe His Leu His Leu Arg Leu Pro Met Ser Val Arg Arg Phe Glu Gln
                835                 840                 845
Leu Glu Leu Arg Pro Val Leu Tyr Asn Tyr Leu Asp Lys Asn Leu Thr
            850                 855                 860
Val Ser Val His Val Ser Pro Val Glu Gly Leu Cys Leu Ala Gly Gly
865                 870                 875                 880
Gly Gly Leu Ala Gln Gln Val Leu Val Pro Ala Gly Ser Ala Arg Pro
                885                 890                 895
Val Ala Phe Ser Val Val Pro Thr Ala Ala Ala Val Ser Leu Lys
                900                 905                 910
Val Val Ala Arg Gly Ser Phe Glu Phe Pro Val Gly Asp Ala Val Ser
                915                 920                 925
Lys Val Leu Gln Ile Glu Lys Glu Gly Ala Ile His Arg Glu Glu Leu
            930                 935                 940
Val Tyr Glu Leu Asn Pro Leu Asp His Arg Gly Arg Thr Leu Glu Ile
945                 950                 955                 960
Pro Gly Asn Ser Asp Pro Asn Met Ile Pro Gly Asp Phe Asn Ser
                965                 970                 975
Tyr Val Arg Val Thr Ala Ser Asp Pro Leu Asp Thr Leu Gly Ser Glu
                980                 985                 990
Gly Ala Leu Ser Pro Gly Gly Val  Ala Ser Leu Leu Arg  Leu Pro Arg
            995                 1000                1005
Gly Cys  Gly Glu Gln Thr Met  Ile Tyr Leu Ala Pro  Thr Leu Ala
    1010                1015                1020
Ala Ser  Arg Tyr Leu Asp Lys  Thr Glu Gln Trp Ser  Thr Leu Pro
    1025                1030                1035
Pro Glu  Thr Lys Asp His Ala  Val Asp Leu Ile Gln  Lys Gly Tyr
    1040                1045                1050
Met Arg  Ile Gln Gln Phe Arg  Lys Ala Asp Gly Ser  Tyr Ala Ala
    1055                1060                1065
Trp Leu  Ser Arg Asp Ser Ser  Thr Trp Leu Thr Ala  Phe Val Leu
    1070                1075                1080
Lys Val  Leu Ser Leu Ala Gln  Glu Gln Val Gly Ser  Pro Glu
    1085                1090                1095
Lys Leu  Gln Glu Thr Ser Asn  Trp Leu Leu Ser Gln  Gln Gln Ala
    1100                1105                1110
Asp Gly  Ser Phe Gln Asp Leu  Ser Pro Val Ile His  Arg Ser Met
    1115                1120                1125
Gln Gly  Gly Leu Val Gly Asn  Asp Glu Thr Val Ala  Leu Thr Ala
    1130                1135                1140
Phe Val  Thr Ile Ala Leu His  His Gly Leu Ala Val  Phe Gln Asp
    1145                1150                1155
Glu Gly  Ala Glu Pro Leu Lys  Gln Arg Val Glu Ala  Ser Ile Ser
    1160                1165                1170
Lys Ala  Asn Ser Phe Leu Gly  Glu Lys Ala Ser Ala  Gly Leu Leu
    1175                1180                1185
Gly Ala  His Ala Ala Ala Ile  Thr Ala Tyr Ala Leu  Ser Leu Thr
    1190                1195                1200
```

-continued

```
Lys Ala Pro Val Asp Leu Leu Gly Val Ala His Asn Asn Leu Met
1205                1210                1215

Ala Met Ala Gln Glu Thr Gly Asp Asn Leu Tyr Trp Gly Ser Val
1220                1225                1230

Thr Gly Ser Gln Ser Asn Ala Val Ser Pro Thr Pro Ala Pro Arg
1235                1240                1245

Asn Pro Ser Asp Pro Met Pro Gln Ala Pro Ala Leu Trp Ile Glu
1250                1255                1260

Thr Thr Ala Tyr Ala Leu Leu His Leu Leu His Glu Gly Lys
1265                1270                1275

Ala Glu Met Ala Asp Gln Ala Ser Ala Trp Leu Thr Arg Gln Gly
1280                1285                1290

Ser Phe Gln Gly Gly Phe Arg Ser Thr Gln Asp Thr Val Ile Ala
1295                1300                1305

Leu Asp Ala Leu Ser Ala Tyr Trp Ile Ala Ser His Thr Thr Glu
1310                1315                1320

Glu Arg Gly Leu Asn Val Thr Leu Ser Ser Thr Gly Arg Asn Gly
1325                1330                1335

Phe Lys Ser His Ala Leu Gln Leu Asn Asn Arg Gln Ile Arg Gly
1340                1345                1350

Leu Glu Glu Glu Leu Gln Phe Ser Leu Gly Ser Lys Ile Asn Val
1355                1360                1365

Lys Val Gly Gly Asn Ser Lys Gly Thr Leu Lys Val Leu Arg Thr
1370                1375                1380

Tyr Asn Val Leu Asp Met Lys Asn Thr Thr Cys Gln Asp Leu Gln
1385                1390                1395

Ile Glu Val Thr Val Lys Gly His Val Glu Tyr Thr Met Glu Ala
1400                1405                1410

Asn Glu Asp Tyr Glu Asp Tyr Glu Tyr Asp Glu Leu Pro Ala Lys
1415                1420                1425

Asp Asp Pro Asp Ala Pro Leu Gln Pro Val Thr Pro Leu Gln Leu
1430                1435                1440

Phe Glu Gly Arg Arg Asn Arg Arg Arg Arg Glu Ala Pro Lys Val
1445                1450                1455

Val Glu Glu Gln Glu Ser Arg Val His Tyr Thr Val Cys Ile Trp
1460                1465                1470

Arg Asn Gly Lys Val Gly Leu Ser Gly Met Ala Ile Ala Asp Val
1475                1480                1485

Thr Leu Leu Ser Gly Phe His Ala Leu Arg Ala Asp Leu Glu Lys
1490                1495                1500

Leu Thr Ser Leu Ser Asp Arg Tyr Val Ser His Phe Glu Thr Glu
1505                1510                1515

Gly Pro His Val Leu Leu Tyr Phe Asp Ser Val Pro Thr Ser Arg
1520                1525                1530

Glu Cys Val Gly Phe Glu Ala Val Gln Glu Val Pro Val Gly Leu
1535                1540                1545

Val Gln Pro Ala Ser Ala Thr Leu Tyr Asp Tyr Tyr Asn Pro Glu
1550                1555                1560

Arg Arg Cys Ser Val Phe Tyr Gly Ala Pro Ser Lys Ser Arg Leu
1565                1570                1575

Leu Ala Thr Leu Cys Ser Ala Glu Val Cys Gln Cys Ala Glu Gly
1580                1585                1590

Lys Cys Pro Arg Gln Arg Arg Ala Leu Glu Arg Gly Leu Gln Asp
1595                1600                1605
```

```
Glu Asp Gly Tyr Arg Met Lys Phe Ala Cys Tyr Tyr Pro Arg Val
    1610            1615                1620

Glu Tyr Gly Phe Gln Val Lys Val Leu Arg Glu Asp Ser Arg Ala
    1625            1630                1635

Ala Phe Arg Leu Phe Glu Thr Lys Ile Thr Gln Val Leu His Phe
    1640            1645                1650

Thr Lys Asp Val Lys Ala Ala Asn Gln Met Arg Asn Phe Leu
    1655            1660                1665

Val Arg Ala Ser Cys Arg Leu Arg Leu Glu Pro Gly Lys Glu Tyr
    1670            1675                1680

Leu Ile Met Gly Leu Asp Gly Ala Thr Tyr Asp Leu Glu Gly His
    1685            1690                1695

Pro Gln Tyr Leu Leu Asp Ser Asn Ser Trp Ile Glu Glu Met Pro
    1700            1705                1710

Ser Glu Arg Leu Cys Arg Ser Thr Arg Gln Arg Ala Ala Cys Ala
    1715            1720                1725

Gln Leu Asn Asp Phe Leu Gln Glu Tyr Gly Thr Gln Gly Cys Gln
    1730            1735                1740

Val

<210> SEQ ID NO 7
<211> LENGTH: 15
<212> TYPE: PRT
<213> ORGANISM: Homo sapiens

<400> SEQUENCE: 7

Asn Gly Phe Lys Ser His Ala Leu Gln Leu Asn Asn Arg Gln Ile
1               5                   10                  15

<210> SEQ ID NO 8
<211> LENGTH: 16
<212> TYPE: PRT
<213> ORGANISM: Homo sapiens

<400> SEQUENCE: 8

Asn Gly Phe Lys Ser His Ala Leu Gln Leu Asn Asn Arg Gln Ile Arg
1               5                   10                  15
```